United States Patent [19]
Afeyan et al.

[11] Patent Number: 5,453,199
[45] Date of Patent: Sep. 26, 1995

[54] MOLECULAR IMAGING

[75] Inventors: Noubar B. Afeyan, Brookline; Laszlo Varady, Malden, both of Mass.; Fred Regnier, West Lafayette, Ind.

[73] Assignee: PerSeptive Biosystems, Inc., Framingham, Mass.

[21] Appl. No.: 247,134

[22] Filed: May 20, 1994

Related U.S. Application Data

[62] Division of Ser. No. 860,450, Mar. 30, 1992, Pat. No. 5,372,719.

[51] Int. Cl.$^6$ .................................................. B01D 15/08
[52] U.S. Cl. ................................... 210/638; 210/502.1
[58] Field of Search .................... 210/644, 638, 210/632, 198.2, 198.3, 656, 502.1; 436/530, 501; 435/7.9, 6; 427/220, 301

[56] References Cited

U.S. PATENT DOCUMENTS

| | | |
|---|---|---|
| 4,623,716 | 11/1986 | Stevenson et al. . |
| 4,667,024 | 5/1987 | Sitrin et al. . |
| 4,696,981 | 9/1987 | Harada et al. . |
| 4,722,999 | 2/1988 | Handschumacher et al. . |
| 4,740,306 | 4/1988 | Litwack et al. . |
| 4,859,611 | 8/1989 | Groopman et al. . |
| 4,859,765 | 8/1989 | Nestor, Jr. et al. . |
| 4,963,263 | 10/1990 | Kauvar . |
| 4,970,156 | 11/1990 | Avrameas et al. . |
| 4,996,296 | 2/1991 | Pecht et al. . |
| 4,999,291 | 3/1991 | Souza . |
| 5,004,802 | 4/1991 | Kluft . |
| 5,010,175 | 4/1991 | Rutter et al. . |
| 5,011,777 | 4/1991 | Shoyab et al. . |
| 5,019,270 | 5/1991 | Afeyan et al. . |
| 5,030,352 | 7/1991 | Varady et al. . |
| 5,039,488 | 8/1991 | Kohr . |
| 5,043,278 | 8/1991 | Nagaoka et al. . |
| 5,047,512 | 9/1991 | Handschumacher et al. . |
| 5,049,656 | 9/1991 | Lewis et al. . |
| 5,057,223 | 10/1991 | Della Valle et al. . |
| 5,059,654 | 10/1991 | Hou et al. . |
| 5,077,393 | 12/1991 | Hayashi . |
| 5,079,155 | 1/1992 | Cox et al. . |
| 5,110,833 | 5/1992 | Mosbach . |

FOREIGN PATENT DOCUMENTS

| | | |
|---|---|---|
| 0172580 | 2/1986 | European Pat. Off. . |
| 0173233 | 3/1986 | European Pat. Off. . |
| 2653034 | 10/1989 | France . |
| 90-310223 | 2/1989 | Japan . |
| 8404967 | 11/1984 | Sweden . |
| 89/00130 | 1/1989 | Sweden . |
| WO90/02809 | 3/1990 | WIPO . |
| WO91/11241 | 8/1991 | WIPO . |
| WO92/13447 | 8/1992 | WIPO . |

OTHER PUBLICATIONS

Andersson et al., "Enantiomeric Resolution on Molecularly Imprinted Polymers Prepared with only Non–Covalent and Non–Ionic Interactions", *J. of Chromatography*, 516:313–322 (1990).

Andersson et al., "Molecular Recognition in Synthetic Polymers: Preparation of Chiral Stationary Phases by Molecular Imprinting of Amino Acid Amides", *J. of Chromatography*, 513 (1990) pp. 167–179.

(List continued on next page.)

*Primary Examiner*—Frank Spear
*Attorney, Agent, or Firm*—Testa, Hurwitz & Thibeault

[57] ABSTRACT

Disclosed are chemically-produced specific binding, "molecular imaged" sorbents which reversibly bind a preselected macromolecule by spacially matched multipoint interactions between functional groups synthesized on the surface of the sorbent and functional groups on the surface of the macromolecule. Also disclosed are methods of producing such sorbents. The sorbents typically are high surface area solids comprising surface binding regions which have charged groups, metal coordinating groups, hydrophobic moities, or various combination thereof anchored thereto and spaced in the mirror image of complementary interactive groups on a surface of the macromolecule.

5 Claims, 17 Drawing Sheets

OTHER PUBLICATIONS

Andersson, et al., "Enantiomeric Resolution of Amino Acid Derivatives on Molecularly Imprinted Polymers as Monitored by Potentiometric Measurements", *J. of Chromatography*, 516 (1990) pp. 323–331.

Bock et al., "Selection of Single–Stranded DNA Molecules that Bind and Inhibit Human Thrombin", *Nature*, vol. 355, Feb. 1992, pp. 564–566.

Mehra et al., "Efficient Mapping of Protein Antigenic Determinants", *Proc. Natl. Acad.*, 83:7013–7017 (1986).

Norrlow et al, "Improved Chromatography: Prearranged Distances Between Boronate Groups by the Molecular Imprinting Approach", *J. of Chromatography*, 396:374–377 (1987).

Sellergren, Borje, "Molecular Imprinting by Noncovalent Interactions: Tailor–Made Chiral Stationary Phases of High Selectivity and Sample Load Capacity", *Chirality*, 1:63–68 (1989).

Sellergren et al., "Highly Enantioselective and Substrate–Selective Polymers Obtained by Molecular Imprinting Utilizing Noncovalent Interactions. NMR and Chromatographic Studies on the Nature of Recognition", *J. Am. Chem. Soc.*, 110:5853–5860 (1988).

Sellergren et al., "Molecular Imprinting of Amino Acid Derivatives in Macroporous Polymers", *J. of Chrom.*, 347:1–10 (1985).

Welling et al., "Synthetic Antibody Fragment as Ligand in Immunoaffinity Chromatography", *J. of Chromatography*, 512:337–343 (1990).

MOLECULAR IMAGING

This is a divisional of application(s) Ser. No. 07/860,450 filed on Mar. 30, 1992, now U.S. Pat. No. 5,372,719.

BACKGROUND OF THE INVENTION

This invention relates to solid sorbents having surface defining sites capable of selectively binding a preselected macromolecule, useful in the separation of a target solute from a complex mixture and in various types of analyses. The invention also relates to a family of synthetic techniques useful in fabricating such surfaces.

Adsorption of macromolecules such as proteins to surfaces involves attraction at multiple sites through hydrophobic, electrostatic, and hydrogen bonding. Surfaces used in chromatographic packing materials therefore have a high density of ionic, hydrophobic or hydroxyl containing groups available for this adsorption process. The interface between the surface and adsorbed proteins may cover between about 10–100 surface groups on the sorbent, depending on the surface density of the charged or other groups and on the size of the protein. Adsorption typically occurs through 5 to 10 groups on the surface of the protein, so there is a large excess of surface functional groups. As the surface density of functional groups on a sorbent decreases, the strength of protein adsorption typically decreases rapidly. Although the number of groups on the sorbent surface is more than adequate for binding, the groups are not distributed properly in space.

The effect is illustrated schematically in FIGS. 1A and 1B. In FIG. 1A, the accessible surface area of a protein, depicted at 10, has five dispersed anion groups, all of which lie close to one or more cation groups disposed at high density in a field on the surface 12 of the adsorbent. As shown in FIG. 1B, at lower surface density, the protein will be less avidly bound, as the spatial distribution of the anions on the protein surface do not match up well with the positioning of the cations on the sorbent.

Of course, real behavior differs in several respects from the oversimplified situation depicted, as, for example, 1) charged groups are randomly positioned on the sorbent, 2) adsorption occurs in three dimensions, e.g., the charge pair in the square shown in FIG. 1B may be spaced apart in a direction normal to the plane of the paper, 3) the protein may have cation groups on its surface which will be repelled by the cation surface and 4) there are other physical interactions at work in addition to electrostatic attraction.

This complimentary adsorption phenomenon is used most widely in chromatographic processes involving purification and analysis of analytes exploiting differential sorption properties of solutes in a mixed solution. Those who manufacture chromatographic systems generally seek to make the surface of the sorbent as homogeneous as possible, and to have a high density of functional groups. Complementarity is based on the presence of a single set of functional groups on the sorbent surface being complementary with a subset of the functional groups on the analyte. In adsorption chromatography, for example, silanol groups at the surface of silica are used to associate with solutes through hydrogen bonding. This generally is achieved in an organic solvent where hydrogen bonding is strong. In ion exchange chromatography, as noted above, a charged surface interacts with a molecular species of opposite charge through electrostatic interaction. The driving force for interaction is based in part on enthalpic changes upon binding and in part upon entropic effects from the displacement of water at the surface of both the sorbent and the sorbate. In reversed-phase and hydrophobic interaction chromatography, the entropic effect is exploited to its fullest as hydrophobic molecules are forced against the sorbent surface to minimize their hydrophobic contact area with the relatively polar solvent. Immobilized metal affinity chromatography is yet another example of the participation of complementary functional groups in the adsorption process. In this system, immobilized metal coordination compounds interact in the presence of metal such as zinc or copper with histidine on an accessible exterior surface of a polypeptide. This association causes the differential adsorption of polypeptides based on number and spatial arrangement of histidines. All of these systems exploit a surface having a random high ligand density. No attempt is made to match specific structural features of the molecule with structural features of the sorbent surface.

Affinity chromatography is based on exploitation of biological systems to achieve intermolecular docking and adsorption. In this system, the surface of the sorbent is caused to mimic a biological substance which naturally associates with a polypeptide. Affinity interactions generally are based on multiple phenomenon including electrostatic attraction, hydrophobic interaction, hydrogen bonding, and stereochemical interfit.

Reversible binding interactions between pairs of biological macromolecules such as ligands and receptors or antibodies and antigens have been exploited widely to construct systems taking advantage of the exquisite specificity and affinity of these interactions. Affinity chromatography often involves the immobilization of specific binding protein, previously typically polyclonal antisera, but now commonly monoclonal antibody, to a high surface area solid matrix such as a porous particulate material packed in a column. The feed mixture is passed through the column where the target solute binds to the immobilized binding protein. The column then is washed and the target substance subsequently eluted to produce a fraction of higher purity. Solid material comprising such specific binding surfaces also are used in immunoassay where immobilized binding protein is used to capture selectively and thereby separate an analyte in a sample.

There has been steady, sometimes dramatic improvement in methods for producing specific binding protein useful in such contexts and for immobilizing them on surfaces. Thus, monoclonal antibodies largely replaced polyclonal antisera obviating the need to purify the antibodies from bleedings, enabling epitope-specific binding, and established a technology capable theoretically of producing industrial quantities of these valuable compounds. More recently, advances in protein engineering and recombinant expression have permitted the design and manufacture of totally synthetic binding sites mimicking the antigen binding domains of the natural antibodies.

While this technology is very useful it is not without its drawbacks. The binding proteins are high molecular weight biological macromolecules whose function depend on maintenance of a tertiary structure easily altered upon exposure to relatively mild condition in use or storage. Furthermore, while it is now within the skill of the art to prepare antibodies or their biosynthetic analogs having specificity for a predetermined target molecule, the preparative technique are time-consuming and costly, purification is difficult, and the techniques for immobilizing them onto surfaces at high density while maintaining activity is imperfect. Furthermore, when such specific binding surfaces are used for the purification of substances intended for therapeutic or prophylactic use in vivo, they introduce a risk of contamination of the product by foreign biological material. This complicates quality control, increases the complexity of the design of a purification system, and increases the expense and time required to obtain regulatory approval of the drug.

Molecular recognition is an important phenomenon in biological systems. The area involved in the interface between the surface and the analyte can be as small as 10 to 100 square Å in the case of amino acids and monosacharides and range to as large as thousands of Å in the interface between polypeptides forming quaternary structure. At the level between about 10–100 square Å surface area in the interface, man has been successful in mimicking nature. This is the basis for modern affinity chromatography discussed above. However, the ability to discriminate could be increased by using a broader surface area at the interface.

It is an object of this invention to provide rationally designed, stable, inexpensive to manufacture surfaces on solid materials comprising a multiplicity of site which reversibly, noncovalently bind with high specificity and affinity a preselected target molecule. Another object is to provide such materials adapted for use in various types of analyses involving specific binding which heretofore have been limited to the use of immobilized macromolecules of biological origin. Still another object is to provide solids having surfaces containing specific binding sites useful for both preparative and analytical chromatographic separations, which, as compared with conventional affinity chromatography surfaces, are more durable, useful over a greater range of conditions, and less expensive to manufacture. Still another object is to provide a family of synthetic techniques which permit synthesis of rationally designed surfaces containing a multiplicity of regions which, through a combination of spatially matched electrostatic attraction, hydrophobic interaction, chelation, hydrogen bonding, and/or stereochemical interfit, are capable of binding to any given macromolecular surface.

These and other objects and features of the invention will be apparent from the drawing, description, and claims which follow.

SUMMARY OF THE INVENTION

The invention relates to novel sorbents as compositions of matter and methods of making a sorbent useful for binding a preselected molecule at its surface by complementary functional group interaction. Due to this complementarity, there is a selective, reversible association between the molecule and the surface. This association may be used in the purification of the molecule, in its detection or quantitation, and in its removal from a complex system. The methods for making such specific binding surfaces are termed herein "molecular imaging" methods. The surface is said to be an "imaged surface." Practice of the invention provides high surface area chromatography matrix material, molecular-specific sorbents, and catalytically active surfaces. These materials are synthesized as disclosed herein by covalently adhering, in a way that is geometrically controlled at least in the direction parallel and preferably also in a direction normal to an underlying surface plane, a plurality of charged groups, hydrophobic groups, metal coordination groups, and various combinations thereof, to form a mirror image of groups complementary to them on a molecular surface of a target macromolecule. These groups preferably are spaced about a hydrophilic undersurface rich in hydrogen containing groups and electronegative atoms such as oxygen, nitrogen, phosphorus, or sulfur which take part in formation of hydrogen bonds.

More specifically, in a first aspect, the invention provides a solid material defining a binding surface which comprises a multiplicity of regions capable of selective binding of a preselected macromolecule having a plurality of ionizable groups spaced about its molecular surface. Each of the regions comprise a plurality of charged moieties bonded, preferably covalently bonded, to the surface or a coating adhered to the surface, and disposed in spaced-apart relation within the region in a mirror image and charged inverse of at least a subset of the ionizable groups on the surface of the macromolecule. These regions bind the preselected molecule preferentially to other molecules by virtue of the spatially matched electrostatic attraction between the surface of the molecule and the binding surface.

In preferred embodiments, the binding surface is substantially free of bound charged moieties in excess of those which bind to the ionizable groups on the preselected molecule. The binding surface preferably comprises a coating adhered to the surface of a solid particulate material useful, for example, in chromatography, and comprising, for example, particulate styrene divinylbenzene. The charged moieties may comprise negatively charged groups such as carboxylate, sulfonate, phosphate, or phosphonate. Carboxyl groups currently are preferred. The charged moieties also may comprise positively charged groups such as primary, secondary, tertiary or quarternary amines. These charged moieties preferably are bonded to the solid matrix or to an adherent coating constituting the binding surface through flexible oligomeric chains anchored to the underlying surface so that the spaced apart charged moieties define a conformationally compliant charged surface, and the charged moieties are disposed at varying distances from the surface of the underlying substrate so as to match, at least to some extent, surface topography of the preselected macromolecular species. Preferably, each binding region on the surface presents an interfacing surface area of at least 50 square Å, preferably at least 500 square Å, and most preferably over 1000 square Å or more. An important advantage of the invention is that the interfacing area of binding can be much larger than that of an antigen-antibody interaction. The binding surface underlying the spaced apart charged residues preferably is an oxygen rich hydrophilic polymer surface. Imaged surfaces may be synthesized to selectively adsorb various biological macromolecules and are well suited for selectively sorbing proteins such as natural or synthetic lymphokines, cytokines, hormones, growth factors, peptides, morphogens, enzymes, cofactors, ligands, receptors, antibodies and other valuable proteins and polypeptides. They may also be designed to sorb analogs of intermediates in organic reactions thereby to produce catalytic surfaces mimicking the behavior of enzymes.

The spatially dispersed charged moieties bonded to the binding surface may be present in combination with one or more hydrophobic patches disposed at a location within the binding region which interface with one or more patches on the surface of the macromolecule. The surfaces also may include one or more metal coordinating moiety disposed at locations in each binding region to form, in the presence of a coordinating metal ion, metal coordinating bonds between the coordinating moiety and an imidazole residue such as histidine exposed on the surface of a macromolecule.

In a second aspect, the invention provides a solid sorbent material defining a binding surface having regions which selectively bind a preselected organic macromolecule through one or more metal coordinating bonds between the sorbent surface and imidazole residues spaced about a molecular surface of the macromolecule. Each region on the binding surface comprises one or more metal coordinating moieties, again disposed in spaced-apart relation within the region in a mirror image of at least a subset of the imidazole residues. In the presence of coordinating metal ions, the surface regions bind the preselected molecule preferentially to other molecules by multipoint spatially matched metal coordination bonds between the coordinating moieties on the sorbent surface and imidazole residues, e.g., histidine residues, on the surface of the preselected macromolecule. This type of surface can bind selectively with high affinity particularly well to proteins having multiple exposed histidine residues.

In still another aspect, the invention provides such a solid material which defines a binding surface comprising regions which selectively bind through multiple hydrophobic patches. Each region on the binding surface has plural hydrophobic moieties, surrounded by hydrophilic surface, bonded to the binding surface and again disposed in spaced-apart relation within the region in a mirror image of at least a subset of the hydrophobic patches on the surface of the preselected molecule. Such imaged regions bind by spatially matched hydrophobic interaction to the molecular surface of the preselected compound preferentially to others.

Imaged surfaces containing multiple regions which exploit various combinations of these effects, and especially those which extend over surface area of 1000 square Å or more, provide powerful, stable binding systems approaching, equalling, or even exceeding the discriminatory capabilities of the binding molecules of the immune system.

The preferred method of fabricating these molecular imaged surfaces also comprise an important aspect of the invention. Broadly, after selecting the target macromolecule, the synthesis of the molecular image on the surface of a solid is conducted by contacting a solution of the preselected macromolecule with a specially derivatized activated surface produced, for example, as disclosed herein, permitting or inducing reaction between certain groups on the surface of the preselected molecule and the derivatized surface, and then converting remaining reactive moieties on the derivatized surface to inactive form. Next, the covalent bonds between the imaging molecule and the surface are cleaved, or the preselected imaging molecule is digested while leaving residues of the macromolecule covalently bound to the surface. Then, the surface is "developed" to convert the remaining residues into matching, covalently attached, charged, hydrophobic, or metal coordinating groups, or by producing charge at each cleavage point. The optimal strategy for imaging a particular macromolecule may be discerned using computerized protein and other macromolecule modeling techniques as disclosed herein.

More specifically, appropriately spaced ionizable groups may be produced on a surface by providing as a starting material a solid having a surface layer of moieties covalently reactive with ionizable groups, contacting the surface layer with a preselected polyaminoacid macromolecule under conditions in which the ionizable groups of the molecule react with the surface by multipoint formation of covalent bonds between at least some of the ionizable groups and the molecular surface, and then digesting the amino acid polymer by hydrolysing peptide bonds, using strong base or enzymatic hydrolysis, leaving an amino acid residue, covalently bonded to the surface, at each position where an ionizable group had reacted. Next, the amino groups or the carboxylic acid groups of each of the bound amino acids is derivatized to leave a charge opposite in sign and in space to the charge of the ionizable groups on the surface of the preselected peptide bonded amino acid polymer. This results in the production on the surface of spatially distributed charged groups in a mirror image and charge inverse of the reacted subset of the ionizable groups on the molecular surface.

The approach to producing spatially specific metal coordinating compounds is similar but distinct. In this case, a solid substrate material having a surface layer of moieties covalently reactive with an organic, nitrogen containing, polycarboxylic acid metal coordinating compound is required. This surface layer may be the same type of surface layer as is used in making electrostatic molecular imaged surfaces. This material is used in a heterogeneous reaction together with the preselected molecule containing an imidazole residue and a metal ion, under conditions to produce multipoint formation of coordinated metal ion links between at least some of the imidazole residues in the preselect macromolecule and molecules of the coordination compound, and to produce covalent bonds between at least a subset of the covalently reactive moieties on the surface of the solid material and the coordination compound. Next, the metal ions are removed from the reaction mixture, e.g., by chelation, to produce on the surface of the material a multiplicity of regions comprising plural, covalently bonded metal coordinating compound molecules spaced apart within the regions in the mirror image of the imidazole residues on the macromolecule.

The approach to producing hydrophobic surface in the binding regions, appropriately located to interact with the macromolecule by hydrophobic attraction, involves prereacting the preselected molecule with an amphipathic molecule. The term amphipathic molecule, as used herein, refers to a molecule comprising a hydrophobic moiety, such as a hydrocarbon, halocarbon, or aromatic residue, which associates with a hydrophobic patch on the target molecule, and a covalently reactive group, such as an amine, carboxylic, aldehyde, or epoxy residue, adapted to react with the activated surface. One then provides a starting material having, e.g., the same covalently reactive hydrophilic surface as is used to derivatize with charged or metal coordinating groups, and reacts this solid starting material with the amphipathic molecule/preselected molecule complex, held together by hydrophobic-hydrophobic interaction. This reaction produces a sorbent comprising hydrophobic bonding interaction sites, which associate with at least a subset of the hydrophobic patches on the surface of the preselected macromolecule, and which are covalently bonded to the surface through the covalently reactive moieties on the solid binding surface and the covalently reactive groups of the amphipathic molecules. The preselected molecule then is desorbed from the surface by breaking the hydrophobic-hydrophobic attraction to yield a surface comprising regions wherein plural, covalently anchored hydrophobic moieties are spaced within a hydrophilic field in the mirror image of the hydrophobic patches on the molecular surface of the preselected macromolecule.

In preferred aspects of the method, high surface area solid material is used, e.g., a perfusive matrix material such as is disclosed in U.S. Pat. No. 5,019,270, and the first step in the manufacturing process is to produce a uniform, adherent, hydrophilic, derivatizable coating about the entirety of the surface of the solid matrix, e.g., in accordance with the method disclosed in U.S. Pat. No. 5,030,352. Next, the coating is derivatized with oligomer chains of reactive monomers, e.g., comprising aldehyde or epoxy groups to produce a field of active filaments. A solution of the imaging macromolecule next is placed in contact with the derivatized, reactive surface of the matrix. As the molecule comes in contact with the derivatized surface, nucleophilic amine groups exposed on the molecule surface covalently react with a subset of the epoxy or aldehyde groups on the surface of the matrix. A schiff base is formed in the case of aldehyde coupling which is reduced to a secondary amine. The support-protein complex next is hydrolysed, breaking peptide bonds linking amino acids in the protein, and all remaining epoxy groups in the case of base catalyzed hydrolysis of the epoxy support matrix. This leaves a single amino acid covalently bonded to the surface through its amino side chain leaving a free amino group and a free carboxylic acid group at each point where amines on the polypeptide reacted with the activated surface. To make an imaged anion surface, one derivatizes the amino terminal of the bound amino acids, e.g., by converting them to amidates using an anhydride, thereby leaving carboxylic acid groups and their characteristic negative charge at each point on the surface corresponding to amino groups on the surface of the polypeptide.

Sorbents comprising cations covalently bonded and spaced in the mirror image of plural exposed anions on the molecular surface of a macromolecule can be produced with an analogous strategy using different chemistry. In this case, one starts with a sorbent surface derivatized with, for example, a terminal amine group having an adjacent vicinal hydroxyl group (—CHOH— CH$_2$—NH$_2$). Upon exposure of the imaging molecule to the surface of in in the presence of a water soluble carbodiimide such as 1-ethyl-3(3-dimethylaminopropyl)-carbodiimide, amide bonds are formed between carboxylate ions on the surface of the macromolecule and the amine groups on the surface of the sorbent. Oxidation with periodate cleaves the remaining —CHOH— CH$_2$—NH$_2$ to produce a bonded aldehyde (—CHO) group. This group will react with any lysine, arginine, or N-terminal amino groups on the macromolecule that are located at the sorbent-macromolecule interface, forming a schiff base. Sodium borohydride is then used to convert the residual surface aldehyde groups to primary alcohols and schiff bases to secondary amines. Next hydrolysis in, for example, potassium hydroxide, leaves an imaged sorbent surface having cationic amine groups bonded to the sorbent surface in locations opposite the anionic carboxylic acid groups on the imaged macromolecule. Electrostatic imaging of anionic species is carried out with molecules that have an excess of anionic functional groups. For this reason, only a smaller number of cationic amino acids are bonded to the surface in this process and will have little effect on the adsorption of anionic species.

To produce mirror imaging points of hydrophobicity to induce hydrophobic-hydrophobic interaction, i.e., a specific binding reverse phase sorbent, one mixes together the imaging molecule having one or more hydrophobic patches on an exterior surface and an amphipathic molecule comprising a hydrophobic moiety, e.g., a hydrocarbon or halocarbon, and an opposing moiety comprising a group covalently reactive with an activated surface of the type described above. For example, the covalently reactive group may be an amine or carboxylate group. When the amphipathic molecule and imaging molecule are brought together in relatively hydrophilic media, the hydrophobic regions associate to exclude water molecules between their hydrophobic contact surfaces. This complex is then reacted as disclosed above such that, at the end of the synthetic scheme, the hydrophobic end of each amphipathic molecule extends through a covalent linkage from the surface of the sorbent and is located in space such that it interfits with a hydrophobic patch on the surface of the imaging molecule. This technique is particularly powerful when the molecule is electrostatically attracted by charge on the surface.

The preferred approach to produce sorbent material having an image surface which binds selectively to macromolecules having imidazole residues on its surface, e.g., proteins having exposed histidine residues, involves reacting the imidazole containing macromolecule in the presence of copper or other metal ion and a metal coordinating compound such as iminodiacetic acid (IDA). This results in formation of a copper coordination complex between imidazole moieties on the surface of the target protein and the IDA moieties. The nucleophilic nitrogen in the iminodiacetic acid moiety then can be reacted with aldehyde or epoxy groups in the reaction schemes noted above so that, at the conclusion of the synthesis, an IDA moiety is covalently bonded to the surface of the sorbent at the precise location in space matching the imidazole residues on the imaging macromolecule. This technique also most preferably is used with charge group matching, but may be used separately.

It will be seen that a key to synthesis of molecular imaged surface is to orient an appropriate surface of the target molecule in face-to-face relation with the sorbent surface. In accordance with the invention, the relationship of the imaging molecule to the sorbent surface may be permitted to occur relatively randomly, in which case a "polyclonal" sorbent will be produced, i.e., one in which the multiplicity of binding regions on the sorbent surface contain the mirror images of different presented surfaces of the macromolecule. However, sorbents having a higher frequency of regions imaged to a given face of the imaging molecule can be produced by using several strategies, e.g., taking steps to assure more consistent orientation of the molecule during early stages of the imaging process, or using peptide analogs of a surface region of the macromolecule sought to be imaged. Thus, for example, the presence of antichaotropic salts such as sodium sulfate in solution with the macromolecule at the imaging stage will induce the more hydrophobic face of the target macromolecule to contact the activated sorbent surface. Alternatively, one may include anionic or cationic groups on the activated surface to "dock" a surface of the macromolecule rich in moieties of the opposite charge by electrostatic attraction.

BRIEF DESCRIPTION OF THE DRAWING

FIG. 2A and 2B are "plan view" illustrations looking through an adsorbed protein onto the molecular imaged surface. FIG. 2C is an illustration taken in cross-section showing the nature of the molecular imaged sorbent and the protein adsorbed thereon, and illustrating how the use of oligomeric filaments extending from the sorbent surface can accommodate varying molecular topology on the surface of proteins.

Like reference characters in the respective drawn figures indicate corresponding parts.

The Nature of the Molecular Imaged Surface

The highest specificity of binding between a biomolecule and a surface currently is achieved using affinity interaction between, for example, antibodies and antigen, receptors and ligands, lectins and their receptors, avidin and biotin, etc. Both strength and specificity are important in such specific binding reactions. Affinity based systems often involve binding constants in the range of $10^6$ to $10^9 M^{-1}$, and can be as high as $10^{15} M^{-1}$. Surfaces capable of specific, tight-binding with a preselected molecule currently are produced by exploiting naturally occurring biological binding systems. These systems in turn exploit a combination of electrostatic interaction, hydrophobic-hydrophobic interaction, hydrogen bonding, and stereospecific interfit to achieve high affinity selective binding.

This application discloses how specific binding sites can be produced on surfaces without resort to the production, collection, and attachment of biological binding molecules such as antibodies or receptors. Binding to sorbent surfaces of the invention is selective, i.e., shows a preference for the imaged molecule versus other molecules, and reversible, i.e., involves no covalent bonding. Selective binding, as used herein, means that the surface binds the imaging macromolecule in preference to others. Reversible binding, as used herein, means that binding is achieved without formation of covalent bonds. The chemically defined binding sites of the invention tend to be more stable, resist leaching from the surface, can be reproducibly synthesized, need not expose product to biological materials, and obviate the risk of contamination of product by biomolecules incident to product purification. This process, a type of rational surface design, involves the creation of a specific binding sorbent surface, herein called an "imaged" surface, which is complementary to a surface of a molecule of interest, hereinafter referred to as the "imaging" molecule.

Figure 1A:
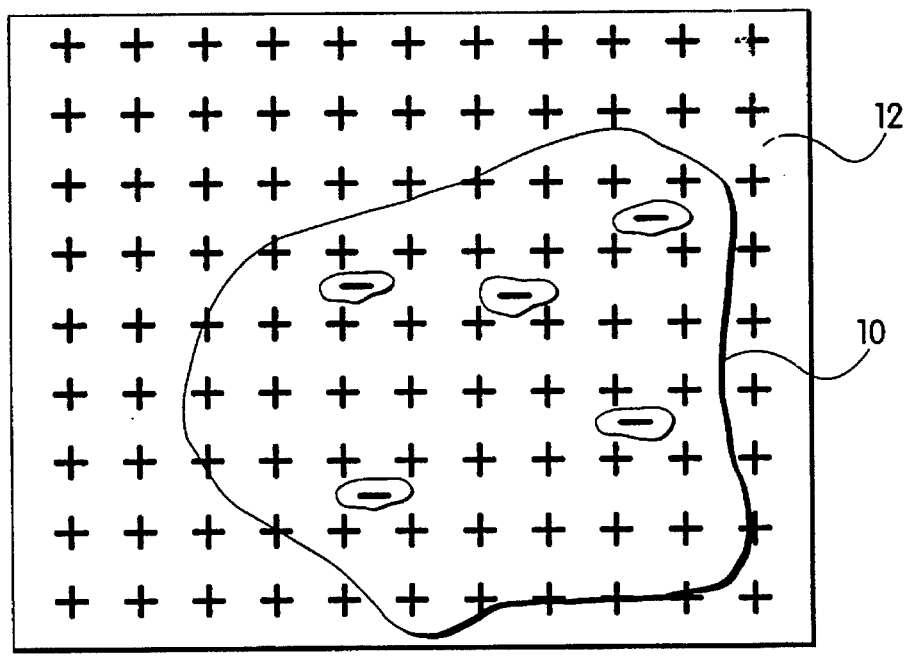
FIGS. 1A and 1B are drawings schematically illustrating the nature of adsorption of macromolecules onto a high density and low density cationic surface, (anion exchange) respectively.
Figure 1B:
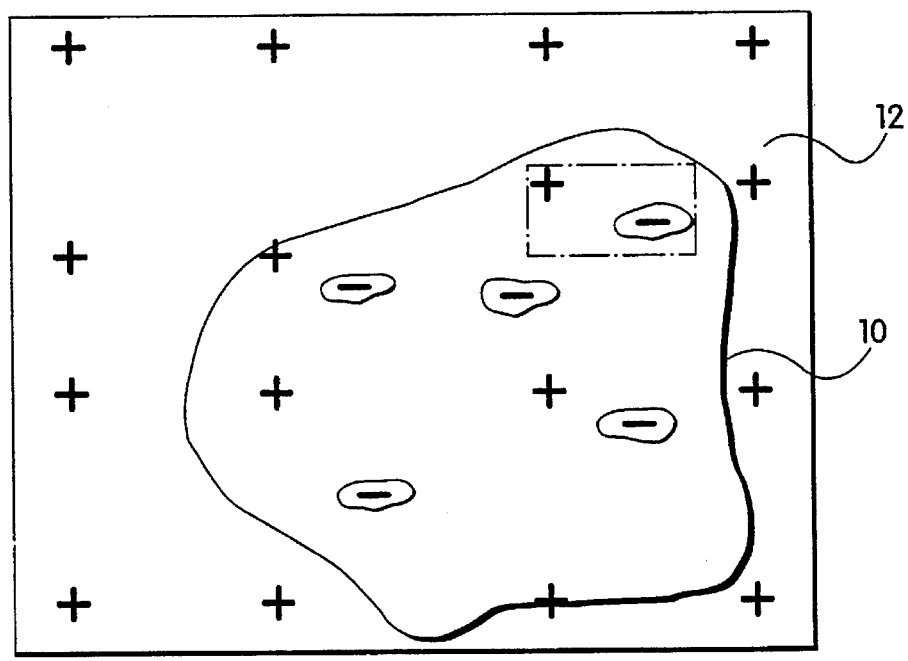

Adsorption of molecules at a surface is based on the existence of complementarity between at least some functional groups on the molecule and those at the surface. FIGS. 1A and 1B, discussed above, exemplify adsorption of a protein onto the surface 12 of a strong cation resin (FIG. 1A) and a weak cation resin (FIG. 1B). As should be apparent, the high density cation sorbent of FIG. 1A will result in a more tightly adhered protein as there is a high frequency of multipoint electrostatic attraction between negative groups on the surface of the protein and positive groups on the sorbent surface 12. Neither the weak nor strong cation exchange sorbent exhibits specificity for any given macromolecule.

Figure 2A:
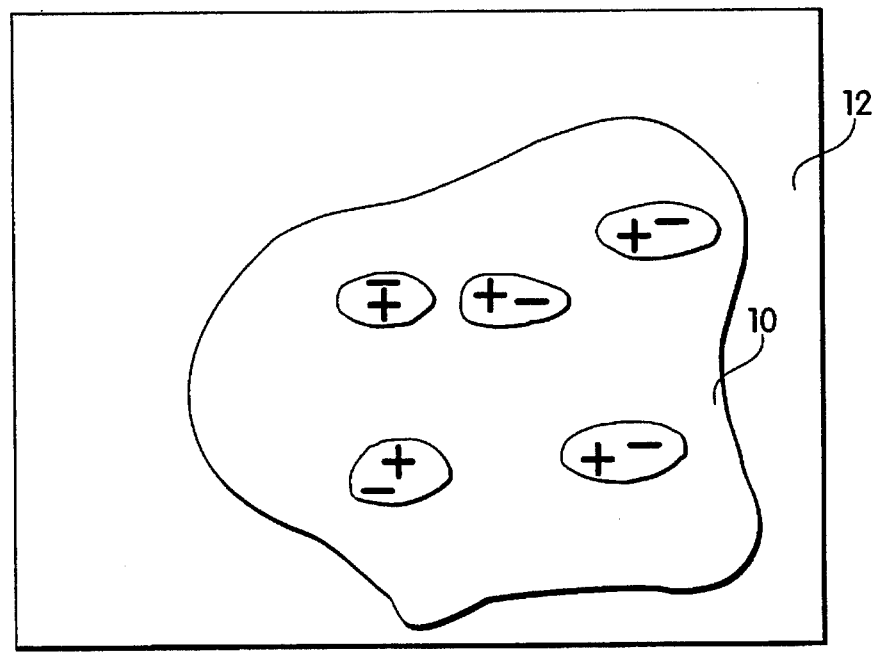
FIG. 2A, 2B, and 2C are illustrations which depict the relationship of a protein or other large macromolecule and a surface imaged as disclosed herein.

In contrast, FIG. 2A depicts a region of a sorbent surface 12 containing only five cationic groups. However, as illustrated, these groups are arranged on sorbent surface 12 such that they are opposite in space to the five negative charges on the surface of the protein 10. This distribution of positive charges in this region of the surface, because it represents the mirror image of the negative charges on the surface of the protein 10, specifically bind protein 10 in preference to other proteins where the charge distribution does not match. Thus, although the charge density of the cationic moieties in the sorbent surface 12 of FIG. 2A is less than the charge density in FIGS. 1A or 1B, protein 10 will adhere to the imaged surface of FIG. 2A with greater affinity, and far greater specificity, than it will to the surfaces in FIG. 1.

Figure 2B:
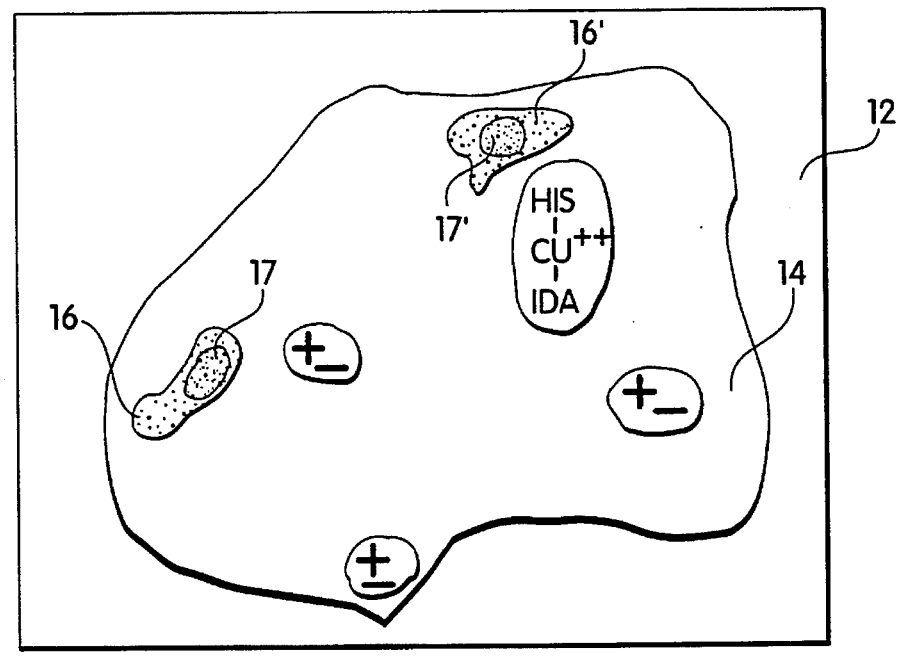

FIG. 2B illustrates still another principle of the molecular imaging technology disclosed herein. Specifically, in FIG. 2B, a different protein 14 is depicted as having a pair of hydrophobic patches 16, 16', three negatively charged groups, and a surface histidine residue. The histidine residue has an imidazole side chain which, as is known, can be attached to a metal coordinating compound by complexation with metal such as copper or zinc. In FIG. 2B, the molecular imaged surface 12 comprises a corresponding pair of hydrophobic patches 17, 17', three appropriately spaced positive ions, and a covalently linked iminodiacetic acid (IDA) metal coordinating molecule disposed opposite the position of the histidine residue on the protein 14. As illustrated, the protein 14 will associate with imaged surface 12 of FIG. 2B with high specificity and affinity. When the protein attains its proper orientation, three positive charges properly spaced on the surface of the sorbent 12, a pair of hydrophobic patches, and, in the presence of copper ions, a metal coordinating bond, all acts simultaneously to hold protein 14 in position. It will immediately be apparent that, for example, surface 12 of FIG. 2B will readily discriminate between macromolecule 14 and macromolecule 10.

Figure 2C:
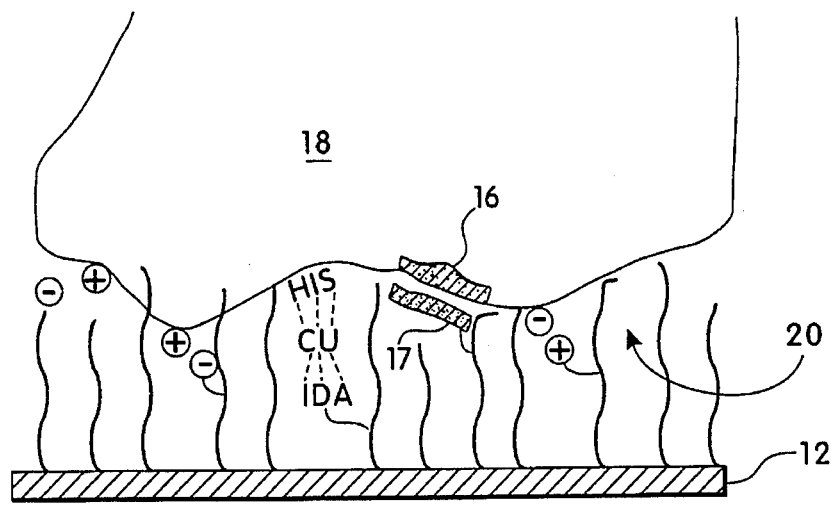

FIG. 2C illustrates still another aspect of the molecular imaging technology disclosed herein. This drawing schematically illustrates a "cross-sectional" view through an imaged surface 12 and yet another different protein, here depicted as 18. The bottom surface 20 of the protein 18 comprises peaks and valleys, or a molecular topology, defined by the three dimensional structure of the macromolecule. Viewed from left to right, the surface of the protein comprises first a pair of cationic groups, e.g., amine side chains in a protein such as those on the lysine or arginine amino acid residues, a histidine residue disposed in a "valley" on the protein surface, a hydrophobic patch 16, and an anionic group, e.g., a carboxylic acid side chain such as is present on amino acid residues like aspartic acid or glutamic acid. In the sorbent of FIG. 2C, random length oligomer chain "filaments" covalently bonded directly to the matrix or to an adherent coating on the matrix comprising the sorbent surface 12, extend upwardly and have appended charged groups opposite in sign to those on the face 20 of the protein 18, a metal chelating group disposed opposite the histidine residue, and a hydrophobic moiety 17 disposed opposite the hydrophobic patch 16 on protein 18.

From the foregoing it should be apparent that proper disposition of charges, hydrophobic patches, and metal coordination groups, both within the plane of a sorbent surface 12 and in a direction more or less perpendicular to the plane, if embodied in a real structure, could produce chemical, as opposed to biological, binding sites of high specificity and affinity. In this case the imaged surface is a copy, counterpart, or likeness of the target molecule displaying matching opposite charge, matching hydrophobic patches, and/or matching metal chelating points which together interact chemospecifically with the imaged molecule and bind selectively and reversibly to the molecule, or at least display significant preferential adsorption of the imaged molecule from a complex mixture.

Several approaches have been envisioned to achieve these goals. The presently preferred approach involves reacting the target macromolecule with an activated surface and leaving behind complementary functional groups. The remainder of the specification will disclose how to make and use such molecular imaged surfaces, and will discuss certain properties of such materials.

The Nature of the Solid Matrix

Sorbents having molecular imaged surfaces produced in accordance with the invention have many uses. Chief among these is affinity chromatography purification procedures, activated sorbents for the removal of a target molecule from a mixture, e.g., a toxin from food, and specific binding assays such as are used widely to detect the presence or concentration of biological molecules, toxins, contaminants, drugs and the like in samples such as water, body fluids, and various plant and animal matter extracts. In many of these uses the solid substrate, or matrix, ideally should have as high a ratio of surface area to volume as is practical. Since it often will be desirable to transport aqueous solutions containing biological molecules such as proteins, carbohydrates, lipids, steroids and the like into contact with the surface to selectively bind or to induce a chemical change in a component in the liquid phase, it is often advantageous to use a rigid solid having a uniform hydrophilic surface and a geometry which permits convective transport of solutes to the imaged surface. A rigid, high mechanical strength material permits high pressure flow without crushing. Perfusive matrices are preferred. Methods for making perfusive matrix materials, the nature and unique geometry of these materials, and various of their advantages are disclosed in detail in U.S. Pat. No. 5,019,270 issued May 28, 1991 and assigned to the owner of this application. The preferred material for fabricating perfusive matrices is polymeric material such as polystyrene divinylbenzene, preferably synthesized as disclosed in the above-referenced U.S. Patent in particulate form. There are various ways of providing on the surface of the inert and hydrophobic styrene based matrix material a hydrophilic coating well suited for interaction with aqueous solutions of biological macromolecules. The currently preferred methods for providing such coatings are disclosed in U.S. Pat. No. 5,030,352 issued Jul. 9, 1991, and assigned to the Purdue Research Foundation of West Lafayette, Ind. The '352 patent discloses how to provide an adherent, crosslinked hydrophilic, easily derivatized coating onto the surface of particulate and other types of matrix material. The coatings are compatible with protein solutions and are extraordinarily versatile, permitting various types of activated groups, oligomers, polymer chains and the like to be fixed to the surface as desired. The disclosures of both the foregoing patents are incorporated herein by reference.

Figure 3A:
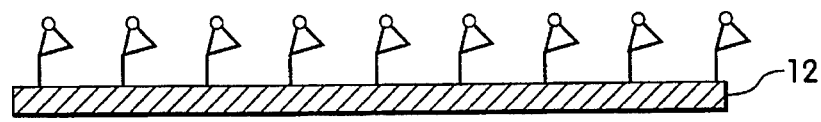
FIGS. 3A, 3B, and 3C depict exemplary activated surfaces of the type useful as a starting point in the synthesis of molecular imaged surfaces of the invention.
Figure 3B:
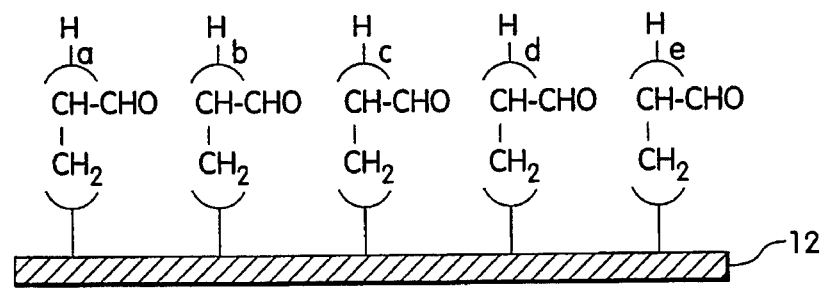
Figure 3C:
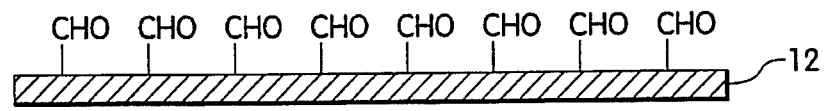

Three exemplary activated surfaces suitable as starting points for the production of the imaged surfaces of the invention are disclosed, respectively, in FIGS. 3A, 3B, and 3C. The first of these represents a portion of a solid matrix 12, shown in cross-section, having a high density of epoxy groups covalently bound to a hydrophilic surface coating adhered to matrix material 12, for example, in accordance with the procedure disclosed in the above-referenced Purdue patent. Matrix material of this type may be produced from POROS® brand chromatography matrix material, e.g., POROS® OH, and are available commercially as POROS® EP from PerSeptive Biosystems, Inc., of Cambridge, Mass. Epoxy groups react with amine groups to produce an alcohol group and a secondary amine covalent linkage. The alcohol group contributes to the hydrophilicity of the surface. The secondary amine linkage forms a strong covalent bond which is exploited as disclosed below to make various types of molecular imaged surfaces.

FIG. 3B discloses another type of activated surface, preferred in many instances, comprising an oligomer of acrolein (acryloylaldehyde), which is characterized by a hydrocarbon backbone having aldehyde groups (CHO)

branching from alternate carbon atoms. This type of activated surface, having oligomers ranging from 1 to 20 monomer units, i.e., a, b, c, d, and e are between about 1 and about 20, can be produced from POROS®-OH, commercially available from PerSeptive Biosystems, Inc., as disclosed herein, by reaction with acrolein in the presence of cerium. Aldehyde groups also react readily with primary nitrogen atoms to produce secondary nitrogen linkages and water in the presence of sodium cyanogen borohydride. Other types of aldehyde activated surfaces are available commercially, e.g., POROS® AL depicted in FIG. 3C. Both the epoxy groups and the aldehyde groups can be further derivatized to form, for example, hydroxyls, carboxylic acid groups, or amine groups using conventional chemistry. These may be used as starting materials in various synthetic schemes as disclosed herein to produce molecular imaged surfaces.

An important aspect of the activated surface 12 of FIG. 3B is that the surface presents a very high density of active aldehyde groups present not only over the entirety of the surface of substrate 12 but also extending away from the surface. Each filament comprises a series of aldehyde side groups appended from a flexible hydrocarbon chain. Reactive moieties on the surface of the imaging molecule can react with the aldehydes buried within or adjacent the surface of the field of filaments, as dictated by the surface shape of the imaging molecule. Furthermore, the filaments can flex and bend laterally to conform to a shape as required by making minor spatial adjustments. This type of activated surface, i.e., a surface having chemically active groups disposed on oligomer units extending upwardly from the surface, permits synthesis of molecular imaged surfaces which can approximate or match the peaks and valleys on the surface of the imaging macromolecule as illustrated in FIG. 2C. It also assures multipoint formation of charged or other groups.

It should be noted that the epoxy and aldehyde groups shown in FIG. 3 are illustrative and preferred, but are by no means the only such groups that can be used. As will be apparent from the disclosure below, the nature of the activated surface groups can vary widely, depending on the particular imaging chemistry used in the manufacture of the imaged surface.

One important chemical feature of these starting materials is the surface density of the surface anchored active groups. If, for example, a pair of charges disposed on a surface of a macromolecule to be imaged are five angstroms apart, then the active groups on the sorbent surface must be at least this close together to be useful in a molecular imaging process. On the other hand, a starting material having 9 or 10 active groups per 100 square angstroms would be operative, although perhaps not optimal, in imaging a molecular surface of, for example, 2000 square angstroms, involving spaced apart charge or other surface features at least 10–20 Å apart. It thus can be seen that the surface spacing of active groups on an imageable surface is directly analogous to grain size in photographic surfaces, and that different surface densities may be used, depending on the resolution required.

The Imaging Molecule

Essentially any macromolecule may be imaged in accordance with the procedures disclosed herein. The term "macromolecule," as used herein, refers to molecules having an imageable surface area of at least 50 square Å. Proteins are currently preferred. Smaller peptides may also be used, and certain of the procedures disclosed herein may be used to form molecular images of glycoproteins, polysaccharides, polynucleic acids and other large molecules. Generally, the interfacing area of the imaged surface and the imaging molecule (i.e., the area of interface between sorbent and sorbate) should be at least about 50 square Å, more preferably 100 Å, and often will exceed 1,000 Å.

It generally is preferable to limit the number of distinct surfaces on a given macromolecule imaged in a given synthesis. This is because it would be possible to create 10–20 different images of the surface of a macromolecule and that each could have a different binding constant. It is also important, particularly in the case of proteins, to avoid during the imaging stage high concentrations of organic solvent, extremes in pH, or elevated temperature. All of these tend to alter the three dimensional structure of the protein or other imaging biological molecule and to create a false image of the molecule, not reflective of its native character.

An important aspect of molecular imaging therefore involves the orientation of the imaging molecule with respect to the surface to be imaged. When using the covalent immobilization synthetic route disclosed herein, molecular orientation can be achieved by using an anti-chaotropic salt such as sodium sulfate, to drive the protein to the surface and promote hydrophobic interaction. Alternatively, charge groups can be included at the surface to orient the imaging molecule in a naturally most favored binding conformation, i.e., one presenting a molecular face rich in the opposite charge.

Another approach to promoting homogeneous imaged binding regions on the sorbent surface is to use peptide analogs of a surface region of the target protein as the imaging molecule. Thus, digested samples of the imaging protein, or randomly generated peptides, may be screened, for example, by affinity chromatography using monoclonal antibody, or using an imaged surface produced as disclosed herein, to obtain a short, e.g., 5–20 amino acid, peptide which mimics the charge or other surface feature distribution of the imaging protein. Methods for producing such peptides are known in the art. Alternatively, rapidly growing data bases storing X-ray diffraction and NMR data from various macromolecules of importance, and programs which display images of proteins and the like based on such data and on amino acid sequence information, may be used to determine sequence of a peptide which mimicks the surface structure of a given macromolecule. Use of such peptides as the imaging molecule may be preferable for cost purposes when synthesizing large quantities of imaged sorbent. They also can provide a source of analogs of short-lived intermediates useful in the preparation of catalytic surfaces, and in any event provide a means of promoting image homogeneity by very significantly reducing the number of surfaces available for imaging during manufacture of the sorbents of this invention.

Preparation of a Molecular Imaged Anionic Surface

In one embodiment, a molecular imaged surface is produced by contacting a protein comprising plural exposed lysine or arginine residues, with their characteristic primary amine side chains, with an epoxide surface such as is illustrated in FIG. 3A, or with the aldehyde group-derivatized surface of FIG. 3B or 3C. After reaction between the aldehydes or epoxides and the amine groups, the protein is digested with strong base, or enzymatically using a mixture of proteolytic enzymes, pronase, or the like, to leave only the corresponding lysine or arginine amino acids at the precise relative locations of these residues in the protein. The positively charged amines are neutralized through acylation leaving a negatively charged carboxyl group at the exact location of a positively charged amine on the imaging protein. Surface hydroxyl groups, which may be esterified during the acylation step, may be converted back to hydroxyl form by hydrolysis. Such an imaged surface will bind the imaging molecule selectively and reversibly through multipoint electrostatic attraction while all other proteins will interact only very weakly as if they were encountering a very weak anion surface.

Figure 4A:
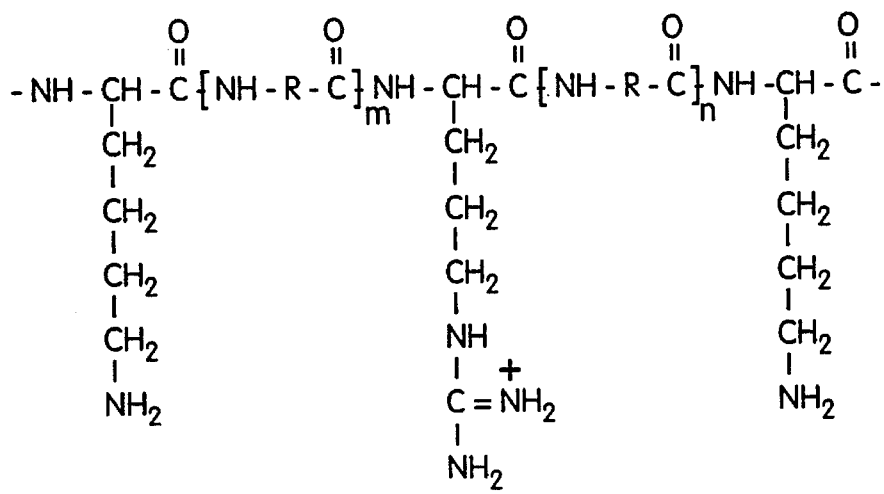
FIGS. 4A–4E are molecular diagrams useful in explaining how to make a molecular imaged surface having anionic groups spaced thereabout in the mirror image of cationic groups on a preselected protein, starting with the activated surface illustrated in FIG. 3A.

Details of how the foregoing synthetic technique is conducted are shown in FIGS. 4A through 4E. Referring to the drawing, FIG. 4A illustrates an activated surface 12 derivatized with plural epoxy groups and, disposed in solution and oriented close to surface 12, a protein, here depicted as amide-bonded amino acids including, for purposes of illustrating the technology of the invention, a central arginine residue flanked by intervening amino acid sequences and a pair of lysine residues. As shown, the lysine residues comprise a side group consisting of $C_4H_8$—$NH_2$; the arginine residue also has a side chain terminating in an $NH_2$ group. The purpose of the synthetic procedure is to provide on the surface 12 negatively charged moieties located in space about surface 12 such that they match the location of the $NH_2$ groups pendant from the side chains of the lysine and arginine residues constituting a portion of the surface of the imaging protein. For ease of explanation, in FIGS. 4B and following, the protein backbone is represented simply by a line extending horizontally, and only the side groups are identified.

Figure 4B:
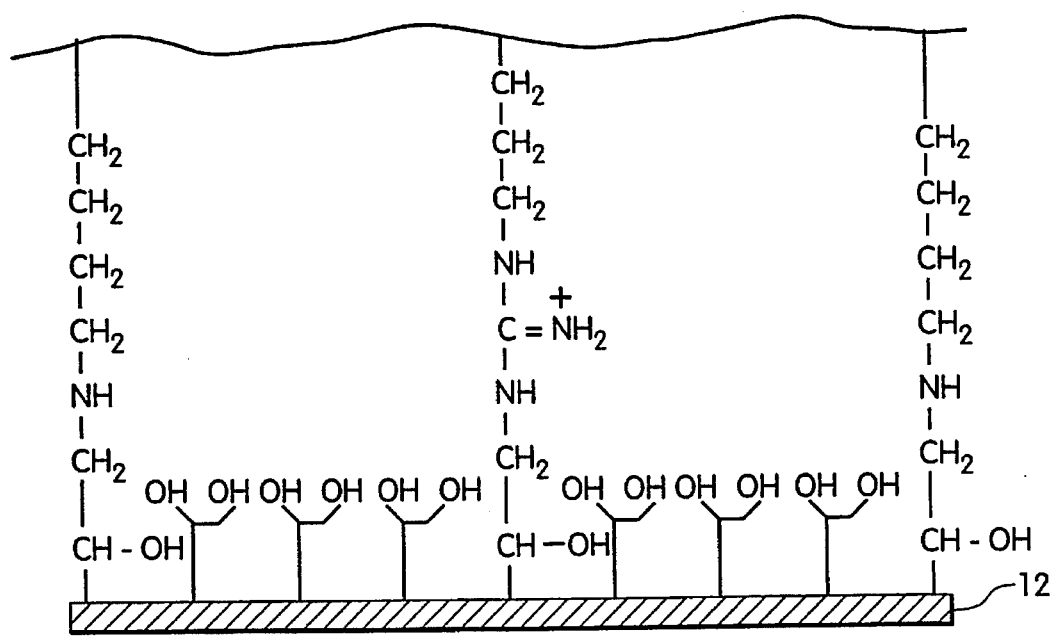
Figure 4C:
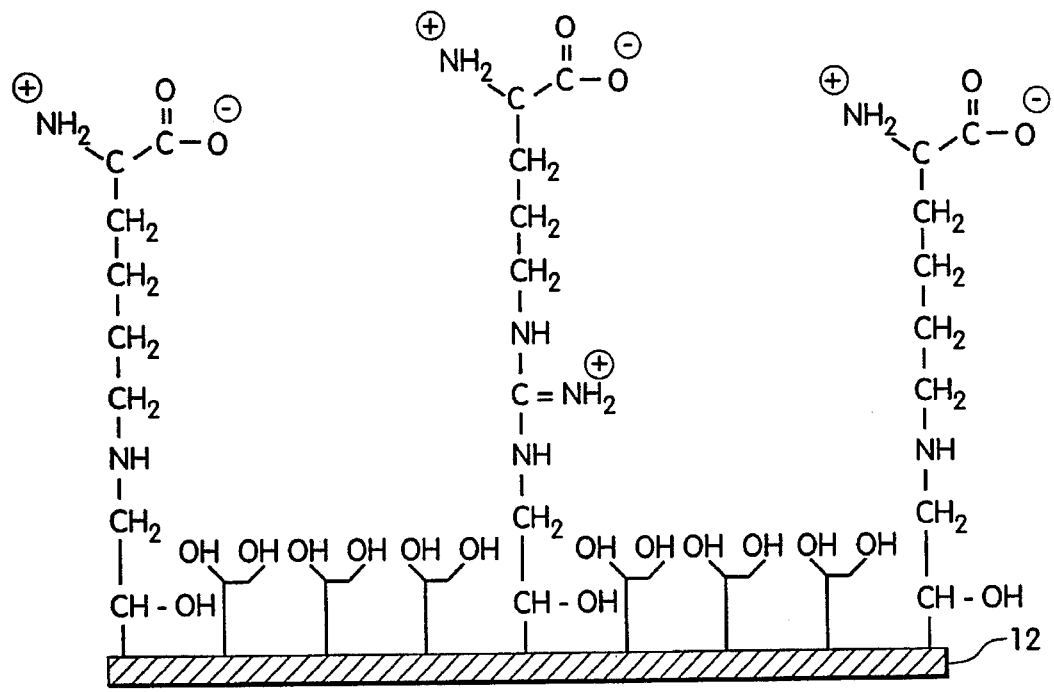
Figure 4D:
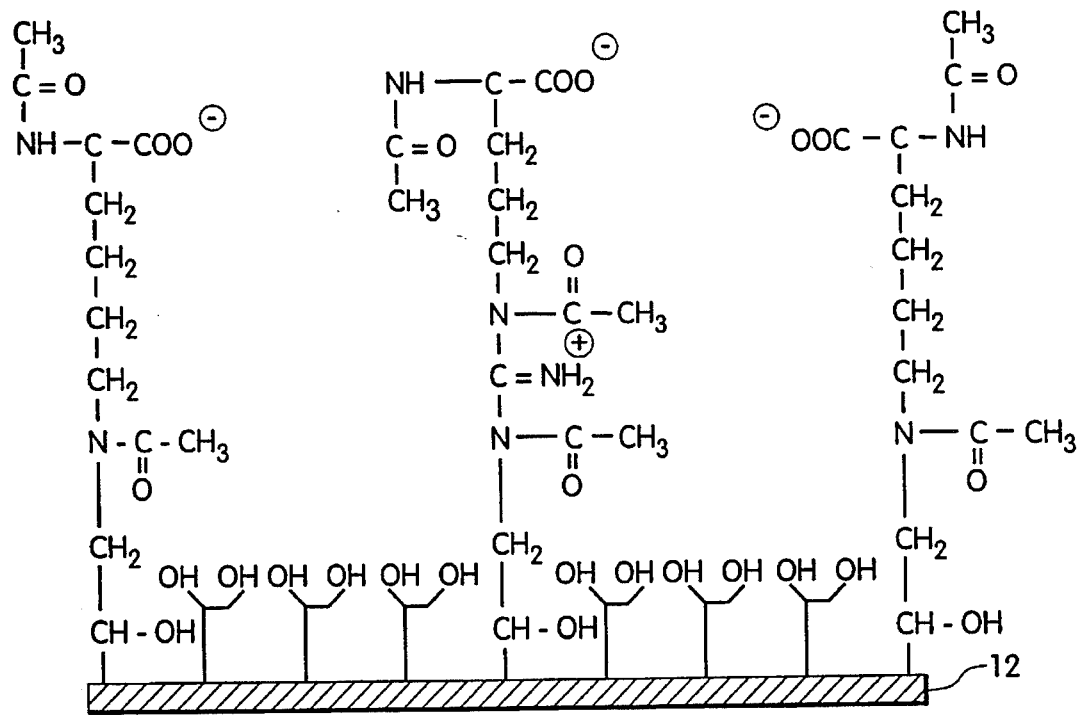

As shown in FIG. 4B, amine groups react with adjacent epoxy groups forming covalent bonds through secondary amines linking surface 12 and the protein. In the presence of weak base, such as sodium phosphate, pH:9, unreacted epoxy groups are opened to form hydrophilic dihydroxyl compounds. Next, the reaction mixture is treated with strong base such as KOH so as to thoroughly hydrolyze the protein. One to three normal potassium hydroxide is suitable for this step. Proteolytic enzymes may also be used. The result is shown is FIG. 4C, wherein only the two lysine and single arginine residues remain. Note the molecular structure on the termini of the covalently-linked chains extending from surface 12 comprise the amino and carboxyl groups characteristic of amino acids. Next, the intermediate imaged surface illustrated in FIG. 4C is treated with, for example, acetic anhydride $(CH_3CO)_2O$ in appropriate solvent such as pyridine, to acylate the amine groups. This results in derivatization and removal of the positive charge region of the amino acid as shown in FIG. 4D, leaving behind the negatively-charged carboxylic acid groups located precisely opposite the amine groups on the protein originally used to initiate the imaging procedure.

Figure 4E:
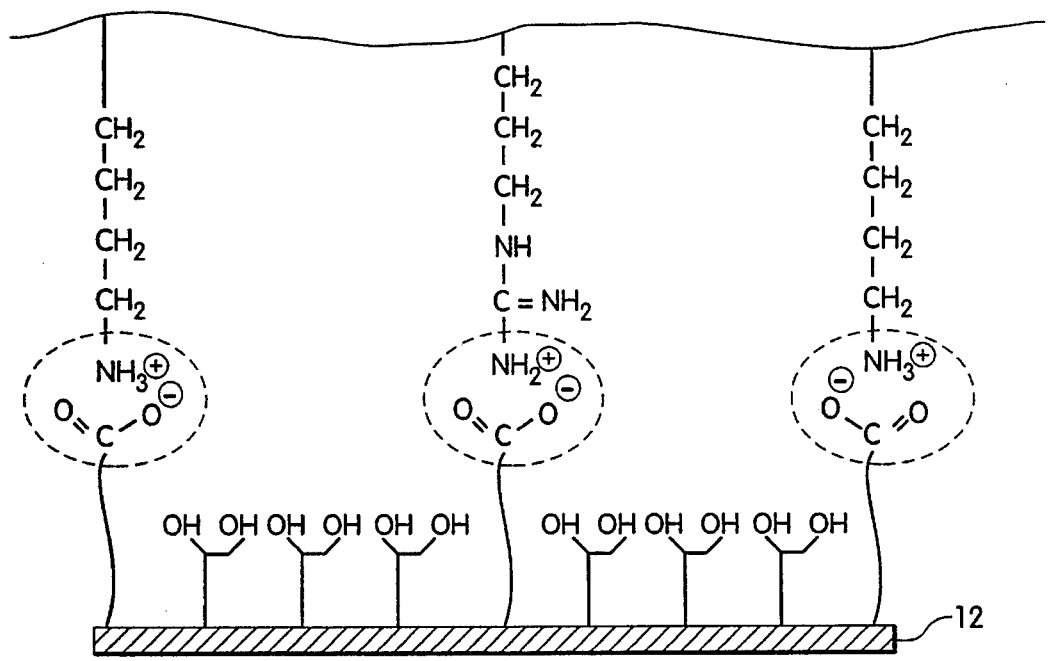

FIG. 4E illustrates the function of the imaged surface. As shown, the imaging protein presented together with other solutes in solution, when encountering the imaged surface, binds preferentially as the amine group in the lysine and arginine side chains "dock" with the carboxylic acid groups by electrostatic attraction. Thus, the relationship of the molecular imaged surface and the imaging protein is as illustrated in FIG. 2A, i.e., selective sorption occurs by virtue of spatially-matched anionic and cationic groups attached respectively to the imaged surface 12 and the surface of the imaging molecule.

Note also in FIG. 4E that the surface 12 is covered with plural OH groups. These can take part in hydrogen bonding and can increase the affinity constant of binding between the imaging macromolecule and the imaged surface.

Figures 5A, 5B, 5C:
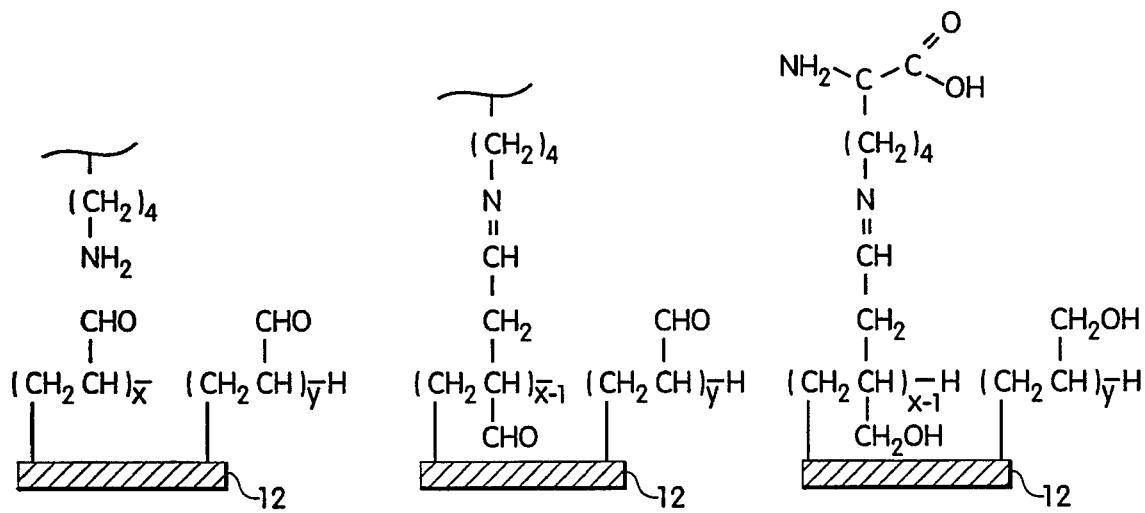
FIGS. 5A–5D are molecular diagrams similar to those in FIG. 4 but using the activated surface of FIG. 3B in place of 3A, and ending with an imaged surface comprising appropriately spaced (both horizontally and vertically with respect to the substrate) anionic charges in the molecular image of the preselected molecule.
Figure 5D:
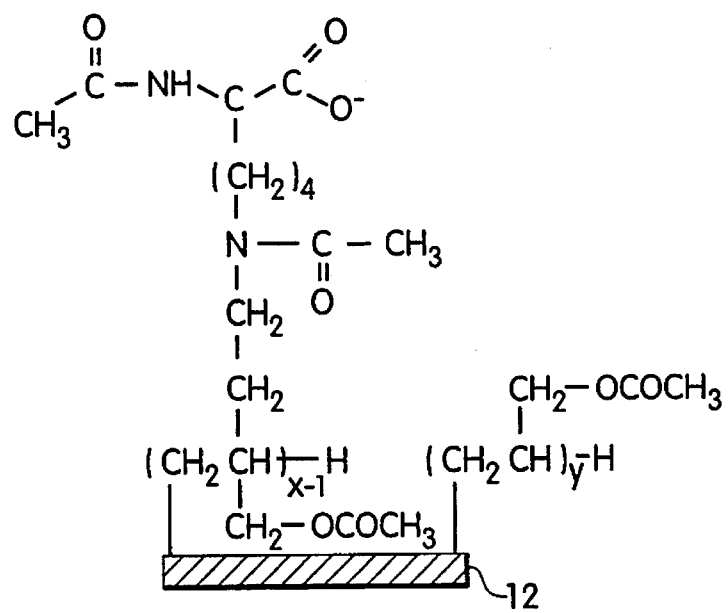

Referring to FIG. 5A through 5D, another series of molecular diagrams similar to those set forth in FIG. 4 are shown which differ from FIG. 4 in that substrate 12 is an aldehyde derivatized starting material of the type illustrated in FIG. 3B. As shown in FIG. 5A, as the amine group of, for example, a lysine side chain, comes into contact with an aldehyde group pendent from a filament some distance from the substrate 12, it reacts to form a secondary amine linking the protein to the surface as shown in FIG. 5B. Residual aldehyde groups are reduced to primary alcohols by sodium borohydride. In the presence of strong base, the peptide bonds linking the amino acids of the protein together are hydrolyzed. This results in a structure such as illustrated in FIG. 5C in which, at each location where the protein had an amino side chain, an amino acid residue remains with its characteristic amine and carboxylic acid groups. The structure next is treated to acylate the amine groups using an acylating reagent such as acetic anhydride to produce the structure of FIG. 5D having a negatively charged carboxylic acid located on surface 12 in position to mate with the various amine groups on the exposed side chains of the imaging protein.

AS noted above, orientation of an imaging molecule prior to or during the reactive imaging step can be accomplished by either hydrophobic or electrostatic interaction. An advantage of the electrostatic interaction is that it will provide an orientation which will maximize the number of interfacing charged sites involved in the synthesis. FIG. 6 illustrates one example of this type of reaction scheme which, in this case, allows electrostatically oriented reactive imaging in production of the imaged surface comprising plural, spaced apart anions.

Figure 6A:
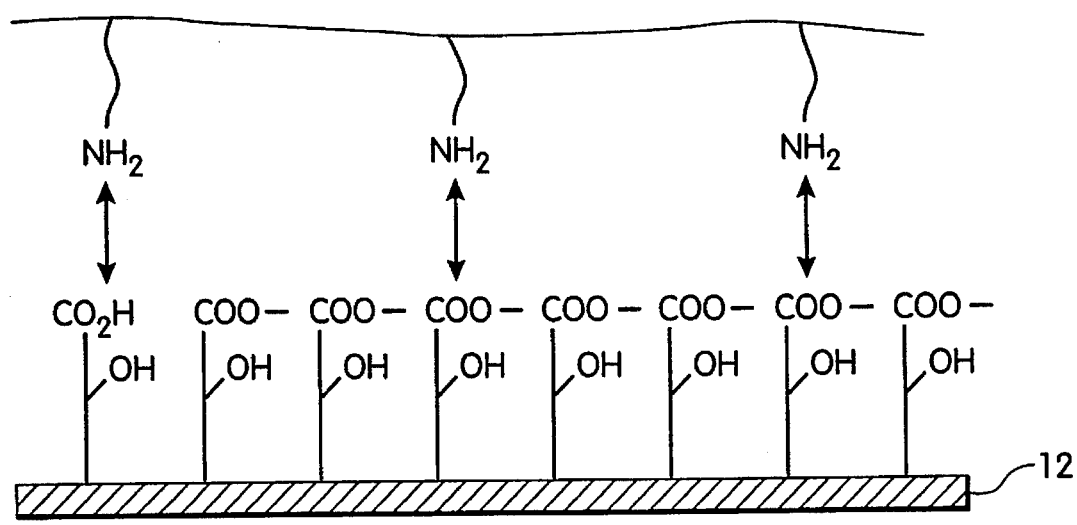
FIGS. 6A–6E are molecular diagrams illustrating how to make a molecular imaged surface beginning with an activated substrate comprising a high density of anionic, carboxylic acid groups whereby the imaging molecule is oriented with respect to the surface by electrostatic forces, i.e., presents its most positively charged surface to the sorbent.

FIG. 6A depicts a protein, here shown simply as lines terminating in amino side groups, interfacing with a reactive surface 12, here comprising alphacarboxyl beta hydroxylic filaments extending upwardly from surface 12. The negative charged polarity of the carboxyl groups and the positive charged polarity of the amine groups on the protein interact to settle the molecular surface of the protein into the activated substrate surface during the imaging procedure. Unlike the previous examples where essentially instantaneous reaction occurs upon contact between an amine group and an epoxy or aldehyde group, in this instance no reaction occurs spontaneously, and equilibrium can be established between the imaging molecule and the surface to be imaged. This promotes production of relatively few separate molecular surface images, i.e., tends to make all of the binding regions more nearly alike in their distribution of charge, and tends to orient the imaging molecule with its most positively charged surface interfacing the sorbent.

Figure 6B:
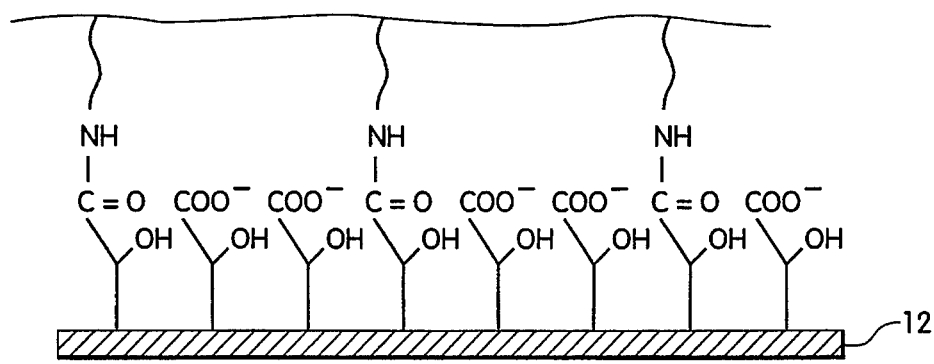
Figure 6C:
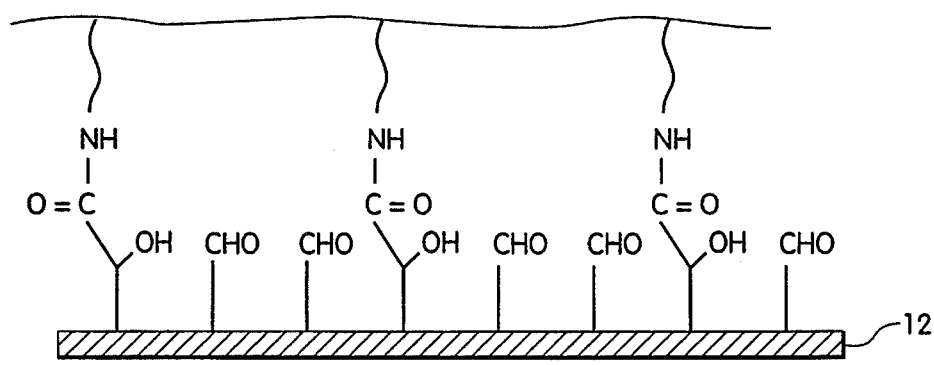
Figure 6D:
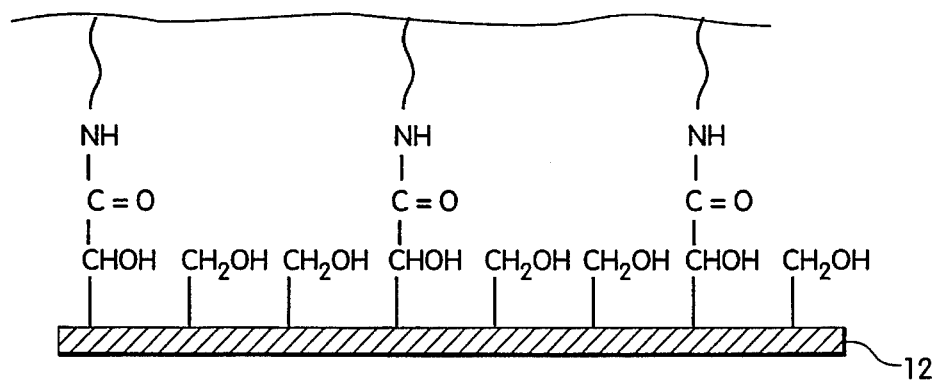
Figure 6E:
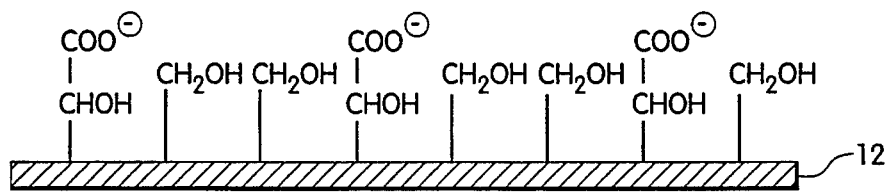

In the presence of EDAC, peptide bonds are formed between the amine groups and the carboxylic acid groups on the sorbent surface as shown in FIG. 6B. Next, in the presence of periodate, free carboxylic acid groups are converted to aldehyde groups (FIG. 6C) and then in the presence of sodium borohydride to alcohol groups (FIG. 6D). Next, strong base such as KOH is used to hydrolyze all peptide bonds leaving carboxylic acid groups covalently bonded to the now imaged surface, spaced thereabout in the mirror image of the amine side groups on the imaging protein.

Preparation of a Molecular Imaged Cationic Surface

FIG. 7A through 7E illustrates how to make still another embodiment of the imaged surface of the invention. In this case, again, the imaging molecule is steered to the surface by electrostatic forces such that the imaged surface of the protein is the area which is most anionic. Formation of the surface begins when a protein, here shown as comprising, from left to right in FIG. 7A, an amino acid such as aspartic acid having an anionic carboxylic acid side chain, and an amino acid such as glutamic acid with another carboxylic acid side chain, and a lysine having a cationic amine group on its side chain. Again, the imaging protein is permitted to reach equilibrium with the surface such that carboxylate groups on its side chains are electrostatically attracted by primary amine groups covalently attached directly to the matrix 12 or to a coating adhering to the matrix. An activated surface comprising a field of amine groups can be synthesized using a variety of techniques. Alternatively, conventional, commercially available, polyimine or polyamine cation exchange resins may be used.

Figure 7A:
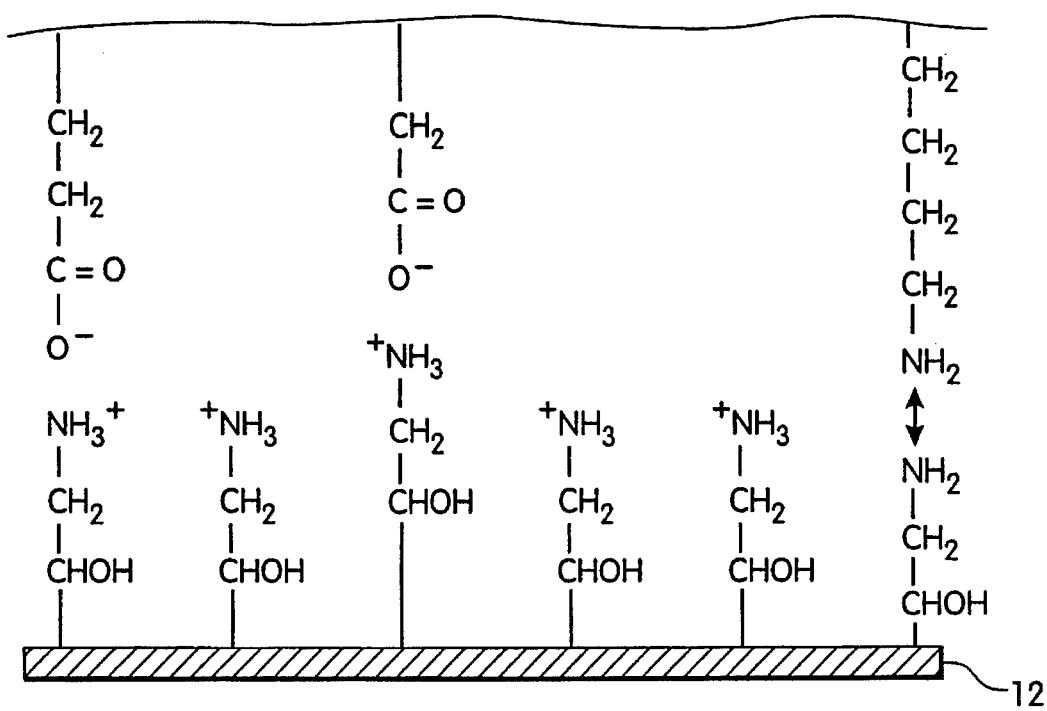
FIGS. 7A–7E are molecular diagrams illustrating how to make a molecular imaged sorbent having plural, spaced-apart cationic groups, and beginning with an imaging macromolecule having plural anionic groups which are attracted electrostatically to the surface in the first stage of the synthesis.
Figure 7B:
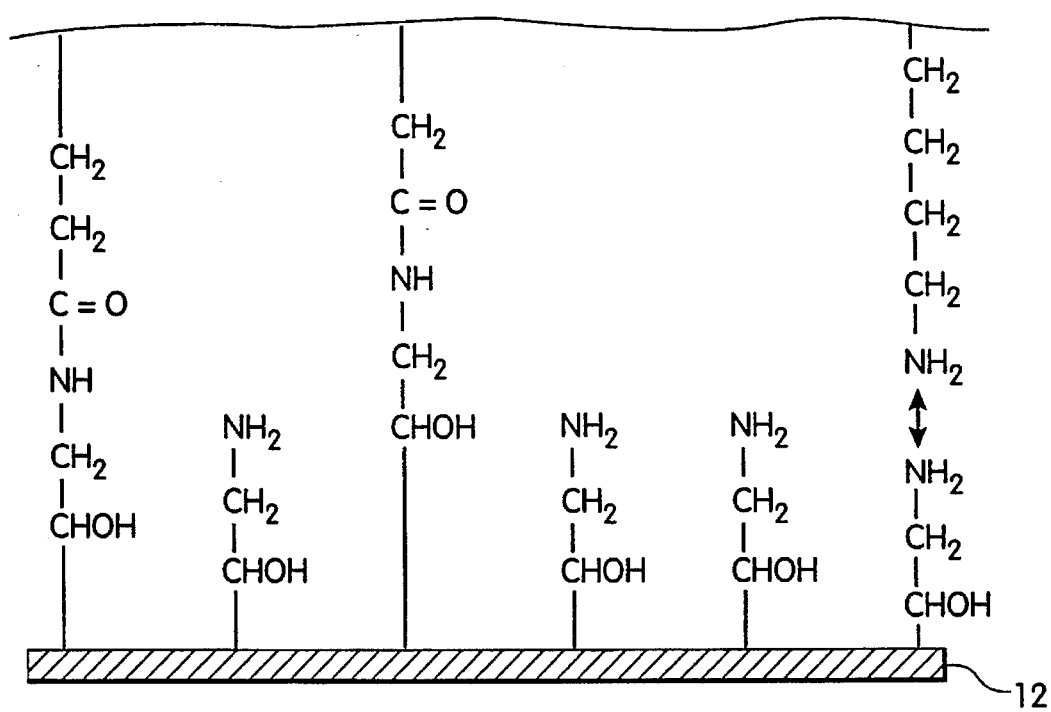
Figure 7C:
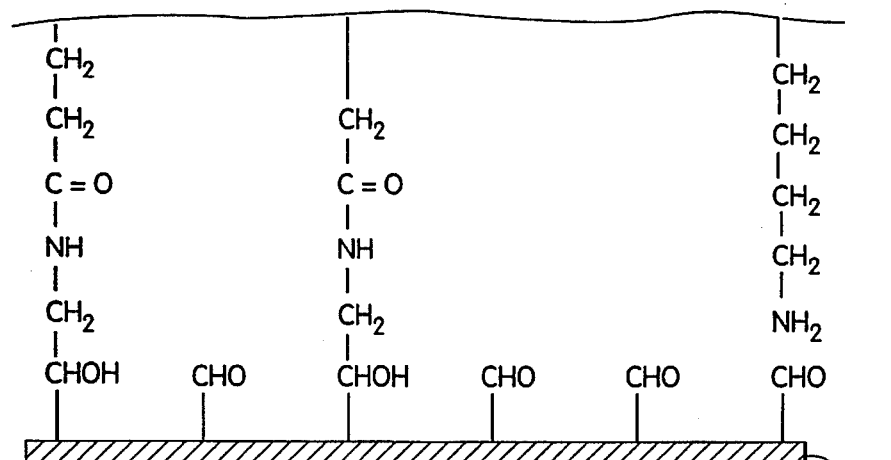
Figure 7D:
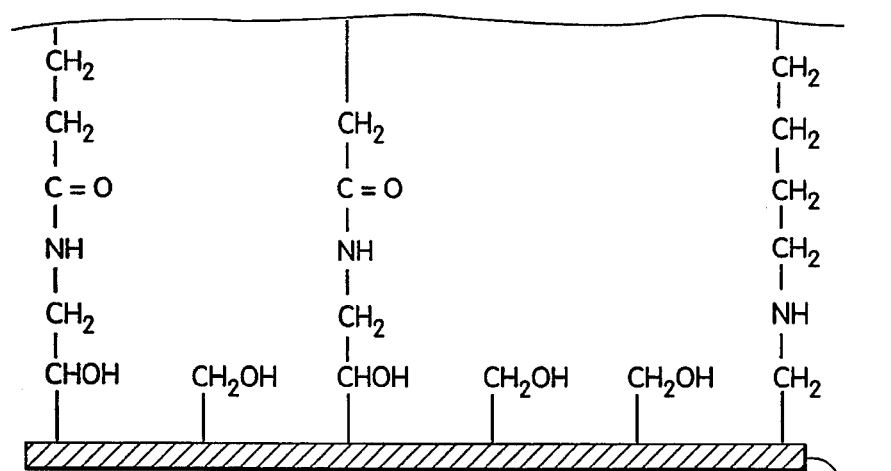
Figure 7E:
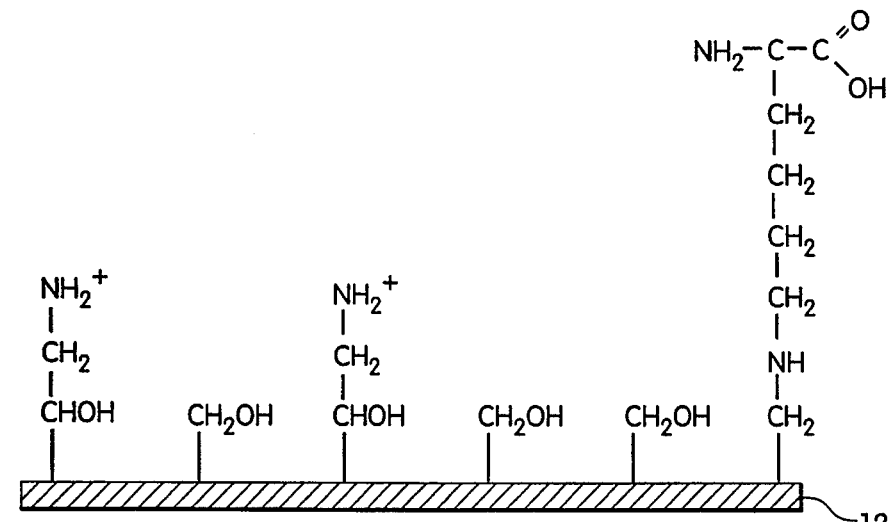

Negative charge on the surface of the protein is attracted to positive charge on the surface of the activated surface. As indicated by a double-headed arrow on the right of FIG. 7A, interfacing amine groups would repel one another. Treatment of the reacting system with EDAC produces amide bonds between carboxylic acid side groups and the amine groups on the sorbent as shown in FIG. 7B. Strong oxidation in periodate ($IO_4$) liberates methylamine from the surface and coverts the terminal alcohols into aldehyde groups as shown in FIG. 7C. Schiff base formation can occur between the resulting aldehyde group and the primary amine group on the lysine side chain provided the density of the aldehyde groups is high enough so that an amine group is in close proximity. Upon treatment with sodium borohydride, the aldehyde groups are converted to alcohol groups, and the schiff base is converted to secondary amine as shown in FIG. 7D. Next, strong based hydrolyzes all peptide bonds leaving, as shown in FIG. 7E, amine group covalently linked to the surface 12 and disposed opposite the carboxylate groups of the side chains of the imaging protein. Where imaging protein originally had an arginine or lysine residue, it becomes linked with the imaged surface.

Figure 8A:
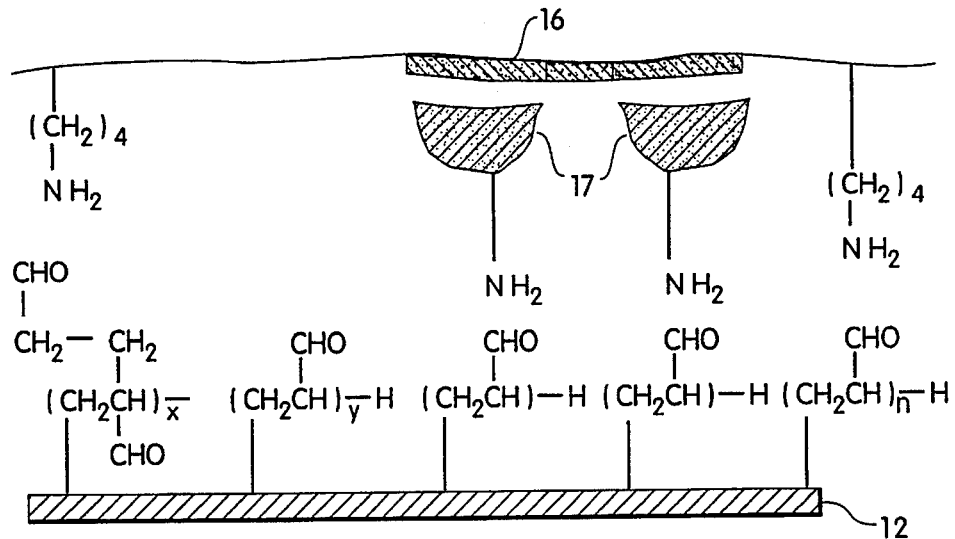
FIG. 8A illustrates a macromolecule having a hydrophobic patch, e.g., a protein having a region high in amino acids with aliphatic or aromatic side chains, in association with two amphipathic molecules comprising a hydrophobic region linked to a primary amine, and disposed in contact with an activated surface of the type illustrated in FIGS. 3B and 5A.
Figure 8B:
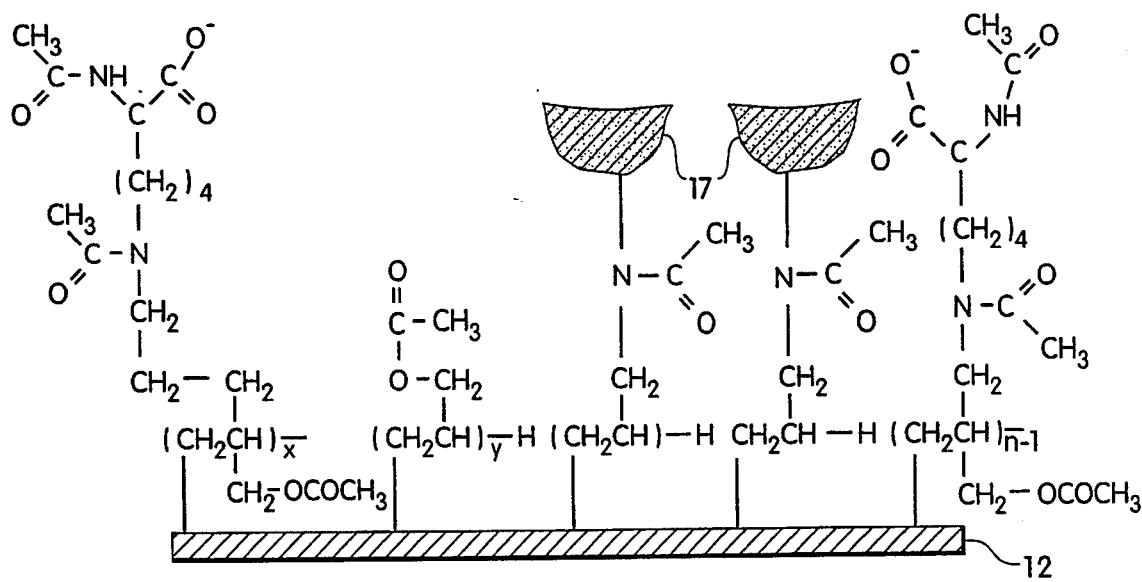
FIG. 8B shows the imaged surface resulting from the starting point of 8A having both anionic groups and a hydrophobic patch disposed in the mirror image of the protein depicted in FIG. 8A.
Figure 9A:
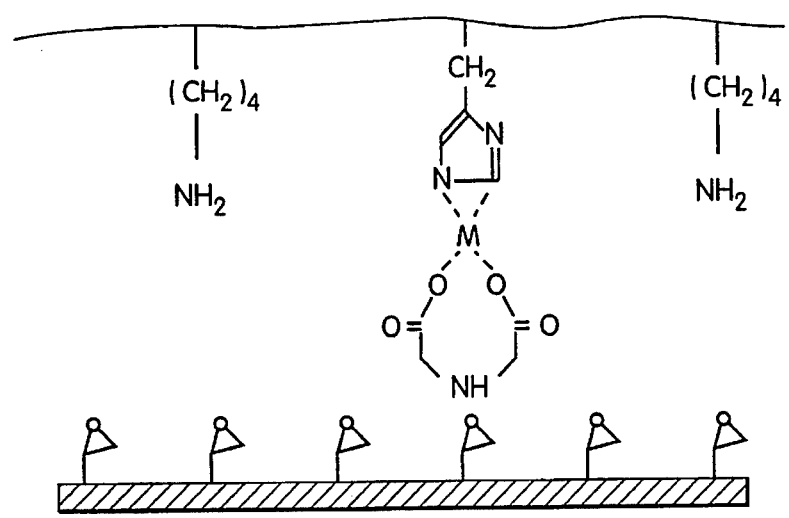
FIG. 9A depicts a macromolecule having a pair of amine side groups and an imidazole side group complexed through a metal ion to an iminodiacetic acid moiety, with the macromolecule and complex disposed adjacent an activated surface of the type illustrated in FIG. 3A.
Figure 9B:
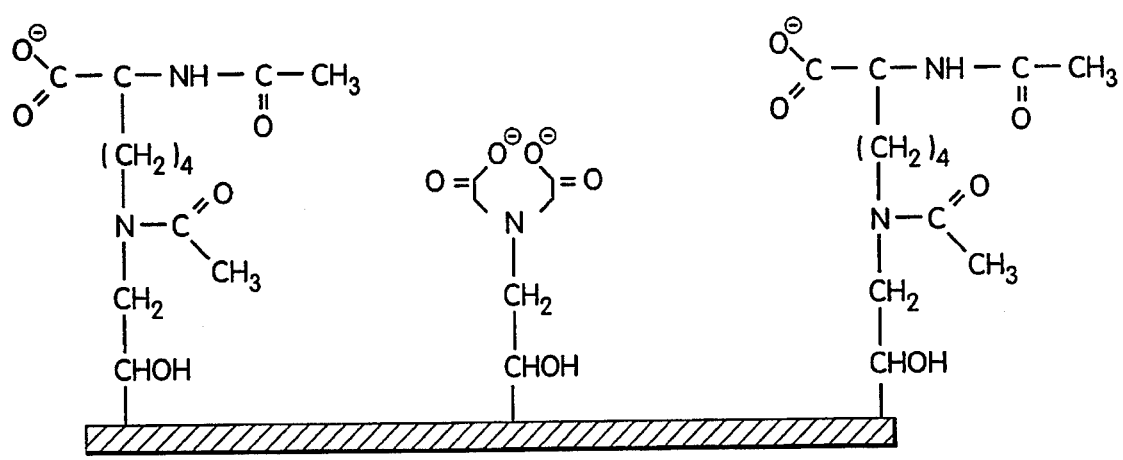
FIG. 9B illustrates a molecular imaged sorbent made by following a preferred synthesis disclosed herein from the starting point of FIG. 9A.
Figure 9C:
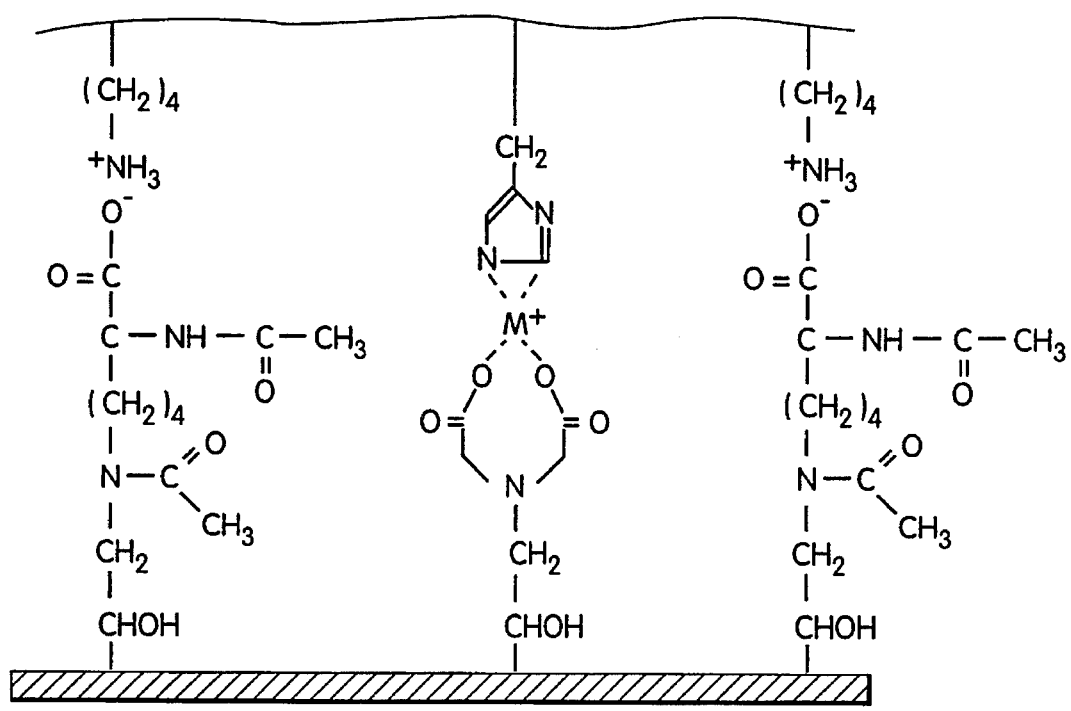
FIG. 9C shows the imaged surface of FIG. 9A comprising a pair of anionic groups disposed in the mirror image of the amine groups on the surface of the macromolecule and an iminodiacetic acid moiety properly disposed with respect to the surface of the imaging protein to form a metal coordinating bond with its imidazole side group and its multipoint electrostatic attraction.

FIGS. 8A and 8B illustrate the method of synthesis of an imaged sorbent having anions and hydrophobic groups covalently linked to the sorbent surface and disposed so as to cooperatively attract a protein having on its molecular surface a plurality of cations and a hydrophobic patch. FIG. 8A shows an activated surface 12 of the type illustrated in FIG. 3B comprising filaments extending from the surface, each of which-have plural pendent aldehyde groups. The imaging protein here is depicted as having a hydrophobic patch 16 disposed between a lysine and an argenine residue.

Prior to mixing the aldehyde activated surface and the protein together to begin the imaging step, amphipathic molecules, here illustrated as amine soaps having a hydrophobic e.g., hydrocarbon, tail 17 and a covalently linked amine group, are mixed together under conditions in which the hydrophobic portion of the soap molecules associate and become embedded in the hydrophobic patch 16 on the surface of the protein. Thereafter, imaging and subsequent synthesis of the image surface is conducted essentially as disclosed above with respect to FIGS. 5A through 5D. The result is shown in FIG. 8B.

Figure 12:
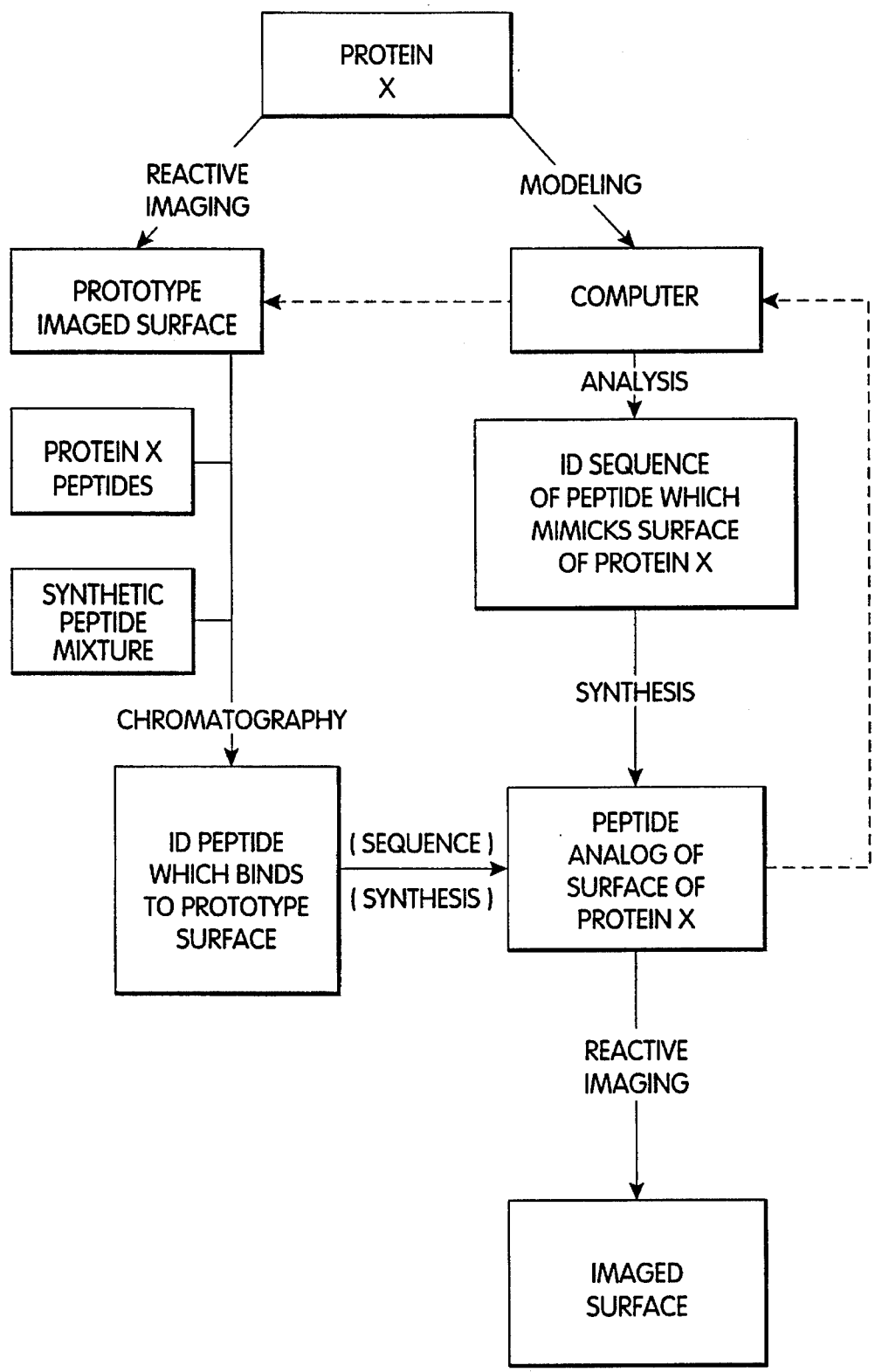
FIG. 12 is a flow chart useful in describing how to optimize imaged surfaces using computer aided design principles.

As illustrated, the result of the synthesis is that anions covalently linked to the surface 12 are disposed in position to interact with cations on the surface of the imaging protein, and hydrophobic groups are positioned to interact by hydrophobic-hydrophobic attraction with the hydrophobic patch on the protein. The hydrophobic amphipathic molecules become bonded to the surface through secondary amine linkages in precisely the same way as the lysine or arginine residues. The amphipathic molecule may comprise, for example, a compound of the formula R-X, where R is a hydrophobic group such as a saturated or unsaturated hydrocarbon, halocarbon, either cyclic, branched, or straight chained, or an aryl group or heterocyclic nucleus, and X is a reactive group which will associate and can form covalent bonds with an appropriate activated surface. X may be, for example, an amine group as exemplified above, or a carboxylate group. When the activated surface comprises a field of amine groups, X may be an epoxy or aldehyde group. This procedure can be used with or without parallel formation of charged groups. It can also be used to produce imaged reverse phase matrix materials that selectively bind predetermined macromolecular species by multipoint matching hydrophobic interaction.

FIG. 9A–9C disclose the synthesis scheme for locating on the surface of the sorbent a metal coordinating compound, here iminodiacetic acid, at a point designed to form a metal coordinating bond in the presence of a metal with an imidizole side chain. FIG. 9A illustrates an activated surface, here exemplified as an epoxy surface of the type in FIG. 3A, interfacing with a protein which, prior to the imaging step, has been mixed with iminodiacetic acid and metal ion such as copper to form a metal coordination complex between the imidizole and IDA groups, shown in the center of FIG. 9A. Flanking the central histidine residue having the imidizole side group is a pair of lysine residues. Formation of the imaged surface occurs using a reaction scheme as illustrated in FIGS. 4A through 4E with the exception that a chelating agent such as EDTA is added to the reaction mixture after hydrolysis of the protein to remove the coordinating metal, thereby leaving a iminodiacetic acid residue opposite in space from the location of the histidine residue on the protein as illustrated in FIG. 9B. FIG. 9C schematically illustrates how the image surface of 9B would interact with the imaging molecule. As shown, in the presence of a metal such as copper (indicated in FIG. 9C as M+) a metal coordinating bond forms between the imidizole residue and the iminodiacetic acid residue at the same time as cations on the surface of the protein and anions on the sorbent surface interact by electrostatic attraction. This procedure also can be used above, to make imaged metal coordinating matrix materials having multipoint metal coordinating bond links, or together with the simultaneous production of hydrophobic interactive functionalities.

The invention will be understood further from the following, nonlimiting examples.

From the foregoing it will be appreciated that there are many alternative strategies for producing a particular imaged surface, and that, to optimize selectivity and affinity for a particular imaging macromolecule, multiple syntheses may be desireable, with each synthesis followed by analysis to guide the next iteration, thereby to more closely attain the desired sorbent properties. An illustration of this general approach appears in the examples below.

It is contemplated in accordance with the invention that computer aided design will play an important role in facilitating development of particular imaged surfaces. An example of how software for modeling protein and other macromolecular structure may be exploited to advantage is shown in FIG. 12. As illustrated, a given macromolecule, here "protein X" can simply be subjected to reactive imaging as disclosed herein to produce a "prototype" imaged surface. If the surface is to be used for low volume procedures, such as analysis, the prototype may suffice. However, if structural data for protein X is known, its three-dimensional configuration and relevant surface properties may be discerned using commercially available molecular modeling softwear in a general purpose computer. Thus, for example, depending on available data on the macromolecule of interest, it may be possible to discover at least the presence, approximate spacing, and relative positions of one or more hydrophobic patches, histidine residues, or charged amino acids on particular surfaces on the macromolecule. This information may be used to aid the chemist in deciding which approach might be successful and which would not, greatly decreasing the work involved. For example, whether metal chelating should be used, whether hydrophobic patch imaging alone may be successful, whether anti-chaotropic salts should be used in the imaging step, and if so, what face of the molecule likely will be imaged, and what features are on that face, all can be determined by modeling. Thus, as in many engineering challenges, computer aided design techniques can give insights which streamline and shorten the design process.

In situations where a large volume of sorbent will be required, or where it is desired to make a highly "monoclonal" imaged sorbent, in accordance with the invention, one can find, analyze, and then synthesize a peptide having a structure which mimicks a surface of a desired macromolecule, and then can use the peptide in a reactive imaging process. Alternative ways to implement this approach also are disclosed in FIG. 12. Thus, peptides generated from partially hydrolyzed protein X, some other protein source, or a synthetic peptide mixture, may be screened for binding to a prototype imaged surface, e.g., using affinity chromatography with differential elution using gradient eluents, to identify a peptide which binds to a prototype surface. This peptide then itself may be used to make a second surface, which in turn is tested for binding to protein X. If the new surface has the desired binding properties, large amounts of the imaging peptide may be synthesized and used to image production quantities of the imaged sorbent. If not, another peptide can be imaged, and the process repeated.

Again CAD can benefit this process. Thus, analysis of a surface peptide sequence may reveal a surface mimicking peptide. It then can be sequenced, synthesized, optionally screened on a prototype imaged surface, and used in reactive imaging to produce a new surface. This new surface can again be tested using protein X, as well as the identified peptide or other peptides. Again, once a surface having the desired properties emerges, it can be duplicated in large volumes using the peptide as the imaging macromolecule, and will bind selectively and with desired affinity to protein X.

EXAMPLE 1. Imaging lysozyme

POROS®-OH (PerSeptive Biosystems, Cambridge, Mass.) was prepared according to U.S. Pat. No. 5,030,352 using an epichlorohydrin-glycidol copolymer that was subsequently crosslinked to produce a matrix rich in surface hydroxyl groups. This material was brominated with $PBr_3$ and subsequently derivatized with sorbitol in the presence of strong base. The resulting surface, rich in diols, was oxidized with $NaIO_4$, then imaged with lysozyme (30 mg/gram of beads) in the presence of 1.6M $Na_2SO_4$, 0.1M phosphate buffer (pH 9.0) for 20 hours in the presence of $NaCNBH_3$. At the end of the reaction, excess aldehyde groups were reduced by $NaBH_4$. The bound protein was hydrolyzed with 4M KOH for 16 hours and subsequently acylated with acetic anhydride for 2 hours. Excess ester groups were hydrolyzed for 2 hours with 0.5M KOH. The result was an imaged sorbent of the type illustrated in FIG. 4E with anions on the surface spaced in the mirror image of amine containing side groups on the surface of lysozyme.

Fourier Transform Infrared Spectrospy (FTIR) was used to analyze the progress of the reaction scheme. Thus, the generated spectra of lysozyme alone, lysozyme immobilized onto the sorbitol activated surface, immobilized lysozyme with a spectrum of the base matrix subtracted out, the surface of the base matrix after hydrolysis, and surface matrix after acylation, all were compared. The spectra of lysozyme alone and the lysozyme on the base matrix were, as expected, very similar. The spectrum after hydrolysis clearly illustrated the absence of lysozyme with loss of the characteristic maximum bands at 3300, 1650, and 1550 $cm^{-1}$. Also, the spectrum of the support after acylation showed a pair of bands at 1750 and 1200 $cm^{-1}$ corresponding to the presence of acetate esters. Lastly, the imaged support was titrated with 0.1M KOH in 5 microliter increments. No measurable ionic capacity on the surface of the sorbent could be detected, indicating that anionic charge density was extremely low, as expected.

The sorbent then was packed in a 4.6×100 mm column, and cytochrome C and lysozyme were applied to the surface with a gradient of increasing sodium chloride from 0 to 1M at pH 6. A cytochrome C peak was eluted from the column at very low ionic strength, followed by a separate peak at only a slightly higher concentration indicating elution of lysozyme.

The conclusion from this experiment, showing rather weak lysozyme binding to the imaged surface, is that while a cation exchange surface was successfully manufactured as indicated by the behavior of the column and by the FTIR spectra, based on the rather low salt concentration (approximately 0.3M) needed to elute the lysozyme in the gradient mode, the density of active groups on the surface of the starting material was probably too low, resulting in the creation of too few points of ionic interaction between the surface of the lysozyme and the binding regions on the sorbent. Accordingly, in an attempt to improve affinity, the experiment was repeated with a higher density of activated groups on the surface of the starting material.

EXAMPLE 2.

Polystyrene divinylbenezene POROS® sorbent was again treated with epichlorohydrin-glycidol copolymer to produce a field of hydroxyl groups about the surface of the perfusive particulate material. This starting material was then suspended in 750 milliliters of water, degassed by vacuum and nitrogen, and added to 25 ml acrolein and 12.5 g cerium sulfate. The mixture was stirred for 8 hours at room temperature under nitrogen, then the beads were washed with water, sulfuric acid, water, and acetone, and dried in a vacuum oven at 60° C. This procedure resulted in the production of a aldehyde activated filamented surface of the type illustrated in FIG. 3B. The surface density of groups available is much higher than the epoxy activated surface of FIG. 3A and Example 1 as the aldehydes not only cover the surface of the POROS® support but also extend from polymer filaments.

Thirty mg of lysozyme were dissolved in 2.5 ml of 0.1M phosphate buffer, pH 9.0. Next, 12.6 ml 2.0M sodium sulfate in 0.1M phosphate buffer, pH 9, was mixed with the lysozyme, and the solution was added to 2 grams of the acrolein activated bead preparation. This mixture was shaken at room temperature for 3 hours, then 100 mg sodium borohydride added with shaking for another hour. The beads then were washed with water, suspended in 50 ml 4M KOH, and stirred with reflux for 16 hours. The beads were then washed with water and acetone and dried in a vacuum oven of 60° C. Next, they were suspended in 25 ml pyridine followed by addition of 25 ml acetic anhydride. The mixture was stirred under reflux for 2 more hours, and the beads were then washed with water and acetone and dried.

The progress of the synthesis was again traced with FTIR. The same series of infrared spectra were produced as discussed above with respect to Example 1. However, titration with 0.1 KOH revealed an ionic capacity of about 1 µM per ml.

As a control, the acrolein derivatized surface was exposed to the reaction scheme described above but in the absence of any imaging agent. Elution experiments on this type of material showed essentially no lysozyme retention on the control surface. Lysozyme could be eluted at less than 100 nM NaCl.

Figure 10A:
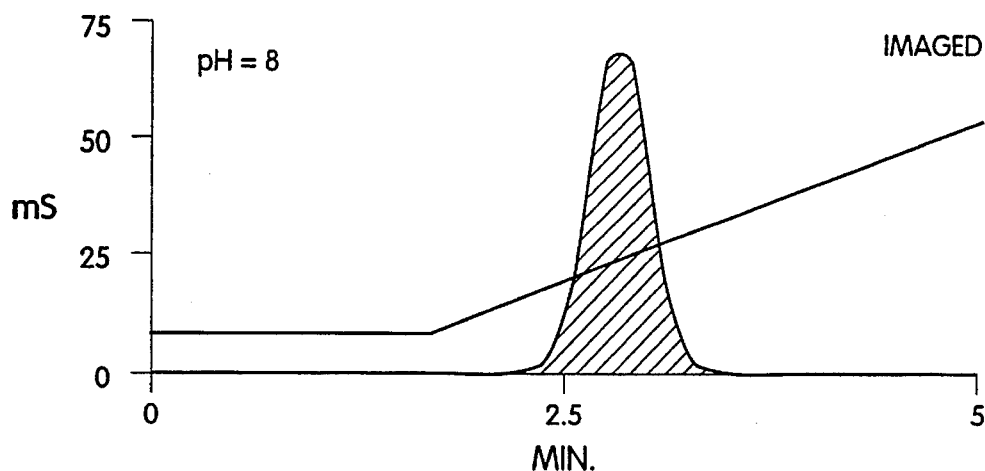
FIGS. 10A–10E are elution profiles illustrating the properties of an imaged column. In each case, the shaded peak represents the imaging molecule, here Lysozyme.

The chromatographic performance of the imaged surface was evaluated by packing a 4.6×100 mm column with the material produced as disclosed above. The plot of a gradient elution of lysozyme at pH 8 is shown in FIG. 10A. The column was loaded with a 100 µl injection of 1 mg/ml lysozyme equilibrated with tris buffer at pH 8. A three minute gradient to 1M NaCl (27 mS conductivity) elutes the bound lysozyme at about 17 mS.

Figure 10B:
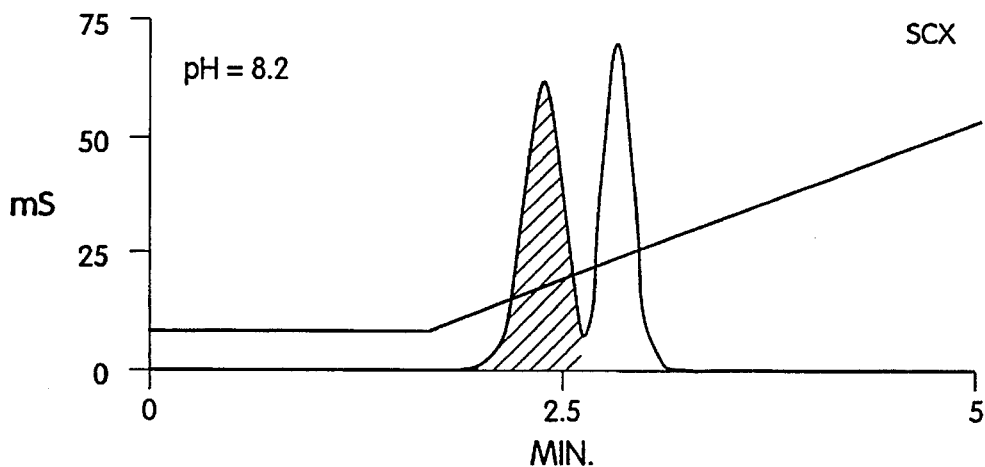
Figure 10C:
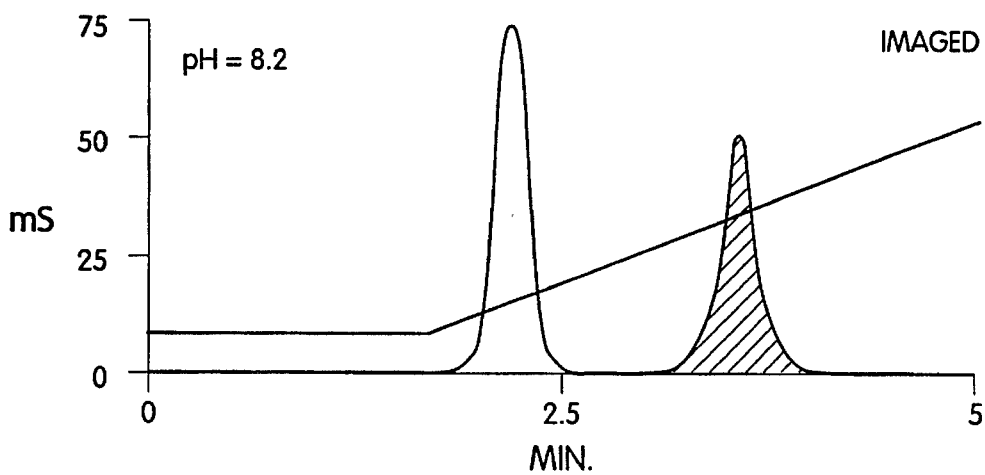
Figure 10D:
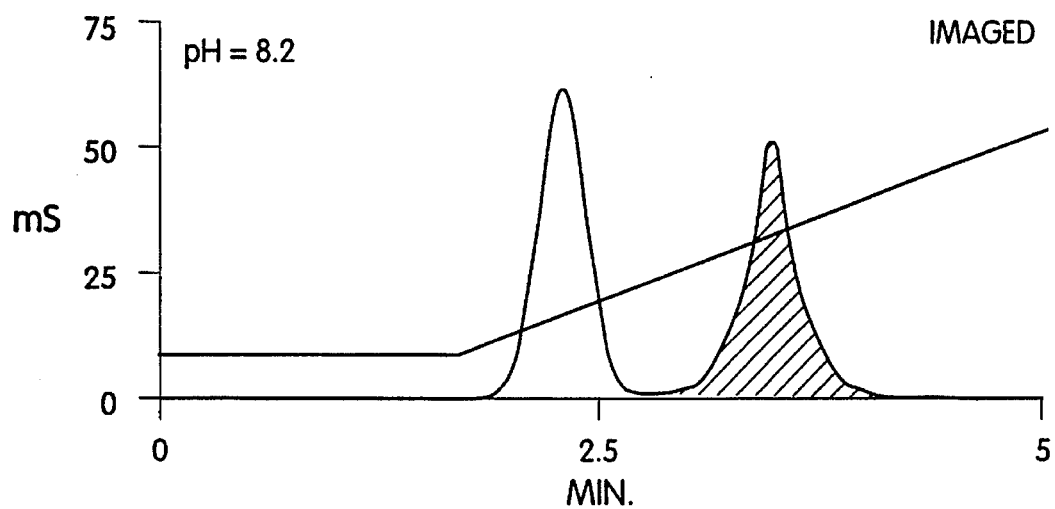
Figure 10E:
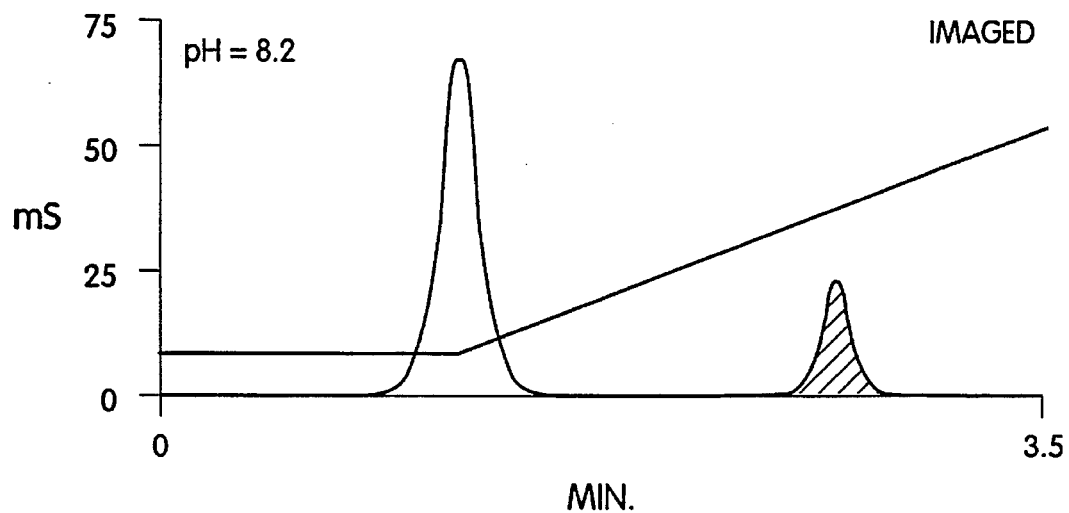

The performance of this lysozyme imaged column can best be illustrated by comparison to a high capacity strong cation exchange column. FIG. 10B shows the gradient separation of lysozyme and cytochrome C on a commercially available cation exchange column (POROS® HS/M). Lysozyme elutes at 0.55M NaCl (15 mS) while cytochrome C elutes at 0.42M NaCl, (11 mS, where 27 mS is approximately equal to 1M NaCl). In contrast, FIG. 10C shows the same test with the lysozyme imaged column. In this case, lysozyme elutes at 0.6M NaCl (16 mS) while cytochrome C elutes at 0.15M NaCl (4 mS). The difference between these two surfaces is that lysozyme is strongly bound to both but cytochrome C binds weakly to the lysozyme imaged column. The same separation profile on the imaged column is illustrated when lysozyme is mixed with other proteins. FIG. 10D shows that chymotrypsinogen binds weakly while lysozyme is bound tightly. FIG. 10E shows that lysozyme is bound tightly while ribonuclease is bound weakly.

Additional work suggests that these results are essentially duplicated at pH 6.2. However, since the functional groups on the surface of the imaged column are weak anionic groups, i.e., carboxyl, one would expect the column to lose its capacity with decreasing pH. As predicted, at pH 4.5, the imaged column does not bind lysozyme well, eluting at the beginning of the gradient, while cytochrome C is completely unretained. This contrasts with the strong cation exchanger used in FIG. 10B which binds both proteins well at pH 4.5.

If one seeks to use the lysozyme imaged column in an on/off affinity mode, a small amount of sodium chloride can be included in the sample and wash buffers. In this case, the imaged column selectively binds lysozyme essentially exclusively from a mixture of lysozyme and cytochrome C provided the feed contains 100 mM sodium chloride. Elution is then conducted by increasing sodium chloride content to 1.0M.

Figure 11:
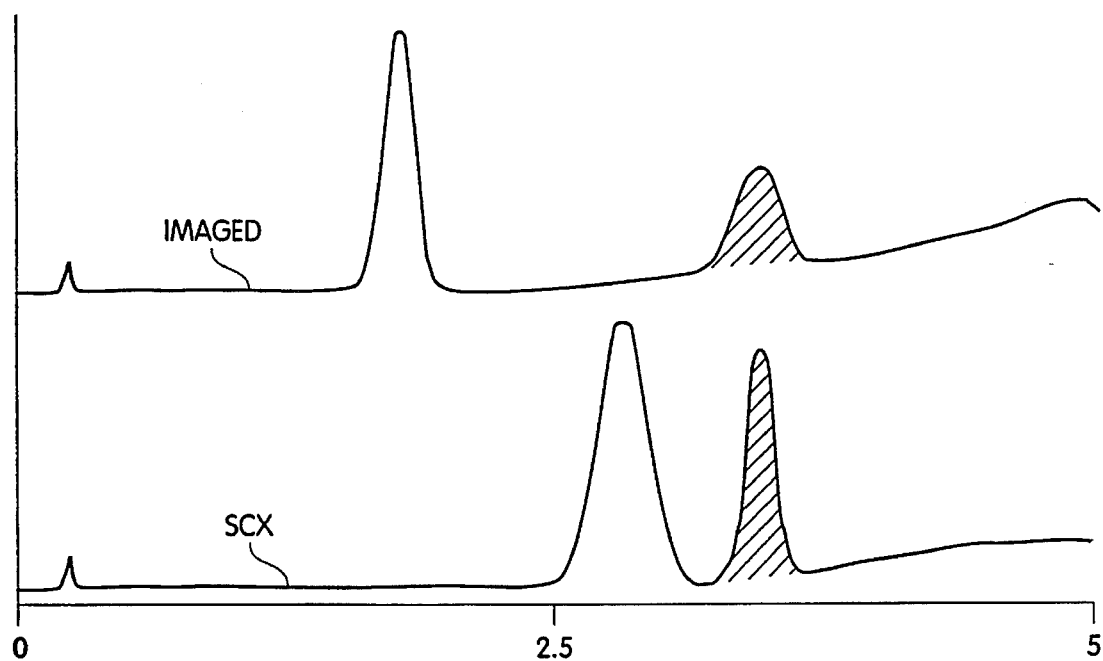
FIG. 11 depicts superposed elution profiles (pH=6.2, 0.0–1.0M NaCl gradient, 5 ml/min in 5 min.) of the same Lysozyme/Cytochrome C mixtures on a Lysozyme imaged column and on a strong cation exchange column.

FIG. 11 shows a direct comparison of gradient elution between lysozyme and cytochrome-C conducted under precisely the same conditions, on a lysozyme imaged column (top plot) and on a strong cation exchange (SCX) column (POROS® HS/M). While lysozyme binds strongly to both surfaces, cytochrome C, with a pI of 9, binds weakly to the imaged surface.

A model of protein adsorption to ion exchange columns has been developed by Regnier et al. (see: The Role of Protein Structure in Chromatographic Behavior Science, Volume 238, page 319, 16 Oct. 1987). This model correlates solute retention to the concentration of eluent by the following equation:

$$k' = \frac{I}{D^z}$$

where k' is a volumetric chromatographic retention factor, I is a constant related to the binding constant, D is the concentration of salt used as eluent, and Z is a constant reflective of the number of interaction sites between the protein and the surface.

Isocratic experiments were performed to map the retention behavior of lysozyme and cytochrome C on strong cation exchange and on the imaged column. Plots of log k' versus D for lysozyme and cytochrome C, followed by linear regression analysis allowed an estimate of the constants I and Z as shown in the table below.

TABLE I

|   | Lysozyme | | Cytochrome-C | |
|---|---|---|---|---|
|   | Imaged | SCX | Imaged | SCX |
| I | 0.25 | 0.03 | 0.006 | 0.003 |
| Z | 2.5 | 5.0 | 2.5 | 4.5 |

As shown, lysozyme interacts with a strong cation exchange surface (SCX) through five sites and with the imaged surface through only 2.5 sites. This indicates either binding through a different contact region on the respective surfaces (consistent with use of the anti-chaotropic salt in the imaging process to salt out the lysozyme) or in low charge density with only 2 to 3 sites per molecule cross sectional area. The latter implies that other solutes of similar size should interact with this surface through at most 2.5 sites. This prediction is verified, at least in the case of cytochrome C, which has a Z number of 2.5 on the anti-lysozyme imaged column.

Although lysozyme binds through only half as many sites on the imaged surface as compared with the conventional strong cation exchange column, the binding constant with the imaged surface is about ten times higher than on the strong cation exchanger. This provides strong evidence for cooperative binding with the imaged surface. The observation is further strengthened by the large difference in ionic capacity between the imaged surface (1 µM/ml) and the strong cation exchange surface (50 µM/ml). Finally, one can compare the relative binding strengths on the two surfaces. On the strong cation exchanger, lysozyme binds ten times stronger than does cytochrome C, through an equivalent number of sites. Lysozyme binds 40 times as strongly to the imaged surface as does cytochrome C. Frontal loading experiments suggest the binding constant between lysozyme and the imaged surface, assuming a Langmuir isotherm to describe the binding process, is about $2\times10^6 M^{-1}$. Compared to antibody antigen reactions, this is on the low end. However, given that only 2.5 sites are involved, it represents a rather strong interaction.

EXAMPLE 3

Bovine serum albumin (BSA) has a pI of 5.7. At pH 6 or 8, its surface therefore will be negative in charge. While BSA has surface amines that can be used in the reactive imaging process described in Example 2, electrostatic repulsion would be expected to interfere with the adsorption of BSA at such an imaged surface. With this premise, BSA was imaged following the procedure of Example 2. FTIR spectra of the reaction scheme indicated that the imaging process has proceeded as expected. The ionic capacity of the material was measured to be about 1.7 μM/ml.

Chromatographic evaluation of this BSA imaged surface was performed in analogous fashion to that described in Example 3. Elution profiles of lysozyme and cytochrome C from this surface showed that lysozyme is weakly retained, needing only about 0.2M NaCl to elute, while cytochrome C is unretained. As predicted, BSA binds to this BSA imaged surface only weakly. It is proposed that electrostatic repulsion is the reason for this behavior. Thus, a cation exchange surface is formed which binds lysozyme through weak cation exchange, does not bind cytochrome C, and binds its target poorly with the mechanistic explanation offered above.

Retention maps were generated to characterize the binding of lysozyme and cytochrome C to this BSA imaged surface in a way similar to that set forth above in Example 2. Binding of cytochrome-C to this surface was too weak to allow a reliable estimate of Z or I. The Z number for lysozyme was 4.2 while the I number was 0.004. and 0.003, respectively. The higher charge density, though not specific for lysozyme, does seem to increase the interaction sites to 4.2. The binding constant for lysozyme onto the BSA imaged surface is understandably low, comparable to that of cytochrome C on the lysozyme image surface.

Binding strength derives in part from the number of interaction sites. As discussed above, an overall binding strength number (I) is related to the binding constant (K) between a solute and a surface ligand. In example 2, K was measured as $2\times10^6 M^{-1}$ for lysozyme and the lysozyme imaged-surface. Based on this measured K and the ratio of I values for various surfaces, one can determine K values for other related surfaces. Assuming that the overall binding constant is the product of individual interaction constants, one can further calculate an average single site binding constant ($K^{1/z}$) as shown in the table below.

TABLE II

| Estimated Average Single Site Binding Constant for Lysozyme on: | |
| --- | --- |
| SCX | 115 |
| Lys-Imaged | 330 |
| BSA-Imaged | 12 |

The foregoing analysis clearly shows the cooperative binding of lysozyme to the lysozyme imaged surface. While the BSA imaged and SCX surface behave similarly, the Lysozyme imaged surface binds 30 times stronger per interation site.

The invention may be embodied in other specific form. Accordingly, other embodiments are within the following claims.

What is claimed is:

1. In the method of separating solutes in a mixture comprising passing the mixture through a matrix which differentially binds individual solutes in said mixture and then desorbing solutes bound to said matrix, the improvement comprising:

providing a matrix comprising,
a solid material defining a binding surface comprising a coating adhered to a surface of said solid material and defining a multiplicity of regions which selectively bind a preselected organic molecule having a plurality of ionizable groups spaced about a molecular surface thereof,
each said region comprising a plurality of charged moieties bonded to said binding surface and disposed in spaced-apart relation within said region in a mirror image and charge inverse of at least a subset of said ionizable groups whereby said regions bind by spatially matched electrostatic attraction to the molecular surface of said preselected organic molecule preferentially to other molecules,
wherein said preselected organic molecule is a target solute in said mixture; and
passing said mixture through said matrix into contact with said surface to preferentially bind said target solute to said binding regions.

2. In the method of separating solutes in a mixture comprising passing the mixture through a matrix which differentially binds individual solutes in said mixture and then desorbing solutes bound to said matrix, the improvement comprising:

providing a matrix comprising,
a solid material defining a binding surface comprising a coating adhered to a surface of said solid material and defining a multiplicity of regions which selectively bind a preselected organic molecule having an imidazole moiety on a molecular surface thereof,
each said region comprising a metal coordinating moiety bonded to said binding surface and disposed in said region in a mirror image position of said imidazole moiety, whereby in the presence of coordinating metal ions, said region binds by multipoint spatially matched attractions including at least one metal coordination bond between said imidazole moieties and said coordinating moieties, to the molecular surface of said preselected organic molecule preferentially to other molecules,
wherein said preselected organic molecule is a target solute in said mixture; and
passing said mixture through said matrix into contact with said surface to preferentially bind said target solute to said binding regions.

3. In the method of separating solutes in a mixture comprising passing the mixture through a matrix which differentially binds individual solutes in said mixture and then desorbing solutes bound to said matrix, the improvement comprising:

providing a matrix comprising,
a solid material defining a binding surface comprising a coating adhered to the surface of said solid material and defining a multiplicity of regions which selectively bind a preselected organic molecule having a hydrophobic patch on a molecular surface thereof, each said region comprising at least one hydrophobic moiety, surrounded by hydrophilic surface, bonded to said binding surface, and disposed within said region in a mirror image position to said hydrophobic patch, whereby said regions bind by spatially matched attractions including at least one hydrophobic-hydrophobic interaction, to the molecular surface of said preselected organic molecule preferentially to other molecules, wherein said preselected organic molecule is a target solute in said mixture; and passing said mixture through said matrix to contact with said surface to preferentially bind said target solute to said binding regions.

4. In the method of separating solutes in a mixture comprising passing the mixture through a matrix which differentially binds individual solutes in said mixture and then desorbing solutes bound to said matrix, the improvement comprising:

providing a matrix comprising, a solid material defining a binding surface comprising a coating adhered to the surface of said solid material and defining a multiplicity of regions which selectively bind a preselected macromolecule having one or more of at least two surface features, spaced about a molecular surface thereof, selected from the group consisting of ionizable moieties, hydrophobic patches, and imidazole moieties, each said region comprising, in a hydrophilic field, a plurality of moieties selected from the group consisting of charged moieties, hydrophobic moieties, metal coordinating moieties, and combinations thereof, bonded to said binding surface and disposed in spaced-apart relation within said region in a mirror image of at least a subset of said at least two surface features, whereby said regions bind, by at least two of a) spatially matching electrostatic attraction between said ionizable moieties and said charged moieties, b) metal coordination in the presence of coordinating metal ions between said imidazole moieties and said metal coordination moieties, and c) hydrophobic-hydrophobic interaction between said hydrophobic patches and said hydrophobic moieties, to the molecular surface of said preselected macromolecule preferentially to other macromolecules, wherein said preselected macromolecule is a target solute in said mixture; and passing said mixture through said matrix into contact with said surface to preferentially bind said target solute to said binding regions.

5. The method of claim 1, 2, 3, or 4, wherein said matrix comprises a perfusive matrix.

* * * * *